United States Patent
Sukumar et al.

(10) Patent No.: US 9,540,694 B2
(45) Date of Patent: Jan. 10, 2017

(54) HEYL AS A THERAPEUTIC TARGET AND A DIAGNOSTIC MARKER FOR NEOPLASIA AND USES THEREFOR

(75) Inventors: Saraswati Sukumar, Columbia, MD (US); Liangfeng Han, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 871 days.

(21) Appl. No.: 12/227,552

(22) PCT Filed: May 21, 2007

(86) PCT No.: PCT/US2007/012182
§ 371 (c)(1),
(2), (4) Date: Jul. 22, 2009

(87) PCT Pub. No.: WO2007/136856
PCT Pub. Date: Nov. 29, 2007

(65) Prior Publication Data
US 2010/0240574 A1    Sep. 23, 2010

Related U.S. Application Data

(60) Provisional application No. 60/801,664, filed on May 19, 2006.

(51) Int. Cl.
*A61K 38/00* (2006.01)
*C12Q 1/68* (2006.01)
*C07K 16/30* (2006.01)
*G01N 33/574* (2006.01)

(52) U.S. Cl.
CPC ......... *C12Q 1/6886* (2013.01); *C07K 16/3015* (2013.01); *G01N 33/574* (2013.01); *C12Q 2600/118* (2013.01); *C12Q 2600/136* (2013.01); *C12Q 2600/158* (2013.01); *C12Q 2600/178* (2013.01); *G01N 2333/4703* (2013.01)

(58) Field of Classification Search
CPC .............. C07K 16/3015; C12Q 1/6886; C12Q 2600/118; C12Q 2600/136; C12Q 2600/178; G01N 2333/4703; G01N 233/574
See application file for complete search history.

(56) References Cited

U.S. PATENT DOCUMENTS 7,544,476 B1 * 6/2009 O'Hagan ............. C12Q 1/6886 435/6.14
7,812,124 B2 * 10/2010 Palm .................... C12Q 1/6886 435/7.1
8,226,943 B2 * 7/2012 Gurney ................ C07K 16/462 424/130.1
2003/0092009 A1 5/2003 Palm
2005/0095607 A1 * 5/2005 Erlander et al. ................... 435/6
2005/0287544 A1 12/2005 Bertucci et al.
2007/0202109 A1 * 8/2007 Nakamura et al. ........ 424/155.1
2008/0206753 A1 * 8/2008 Egan et al. ....................... 435/6

OTHER PUBLICATIONS

Parker et al. Alterations in Vascular Gene Expression in Invasive Breast Carcinoma, Cancer Res. Nov. 1, 2004, vol. 64, pp. 7857-7866.*
Han. Characterization of the Role of HEYL in Angiogenesis and Breast Cancer Development. Mar. 2005. Prepared for US Army Medical Research and Materiel Command Fort Detrick, MD 21702. 21 pages.*
Henderson et al. Genomic and gene expression profiling of minute alterations of chromosome arm 1p in small-cell lung carcinoma cells. British Journal of Cancer. Published online Mar. 22, 2005. vol. 92, pp. 1553-1560.*
Stahlberg et al. Quantitative real-time PCR for cancer detection: the lymphoma case. Expert Review of Molecular Diagnostics. Mar. 2005, vol. 5, No. 2, pp. 221-230.*
Srinivas et al. Proteomics for Cancer Biomarker Discovery. 2002. Clinical Chemistry 48:8, pp. 1160-1169.*
Kretzschmar. Transforming growth factor-beta and breast cancer Transforming growth factor-beta/SMAD signaling defects and cancer. Breast Cancer Res 2000. No. 2, pp. 107-115.*
Wong et al. Real-time PCR for mRNA quantitation. Review. BioTechniques, Jul. 2005, vol. 39, pp. 75-85.*
Stoler et al. Breast Epithelium Procurement from Stereotactic Core Biopsy Washings: Flow Cytometry-sorted Cell Count Analysis. Clinical Cancer Research. vol. 8, pp. 428-432.*
Huang. Detection of multiple proteins in an antibody-based protein microarray system. J Immunological Methods, 2001. vol. 255, pp. 1-13.*
Colland et al. "Functional Proteomics Mapping of a Human Signaling Pathway." *Genome Res.*, Jul. 2004, vol. 14, No. 7, pp. 1324-1332.
Parker BS et al. "Alterations in vascular gene expression in invasive breast carcinoma." Cancer Res. Nov. 1, 2004;64(21):7857-66.
International Search Report, International Application No. PCT/US2007/12182, completed Oct. 3, 2007 and mailed Nov. 28, 2007.

* cited by examiner

*Primary Examiner* — Marcela M Cordero Garcia
(74) *Attorney, Agent, or Firm* — Mintz Levin Cohn Ferris Glovsky and Popeo, P.C.; Peter F. Corless; Christopher R. Cowles

(57) ABSTRACT

The invention generally features compositions and methods that are useful for treating or diagnosing a neoplasia, in particular breast neoplasia. The invention is based in part on the observation that the basic helix loop helix transcription factor HEYL was found to be overexpressed in breast cancer cells. Accordingly, the invention provides therapeutic compositions and methods for altering the levels and expression of HEYL of the invention, thereby treating a neoplasia, as well as compositions and methods for diagnosing a neoplasia.

6 Claims, 19 Drawing Sheets

```
                ****
HES1      SM WRPW RN--------
HES2      GL WRPW ---------
HES3      RV WRPW ---------
HES4      GP WRPW LR-------
HES5      GL WRPW ---------
HES6      SV WRPW ---------
HES7      AF WRPW P--------
HERP1     KPI O PW G---TEVGAF
HERP2     KFY RPW G---TEIGAF
HERP3     KFYHS W VSEITEIGRF
```

Phalloidin staining of actin

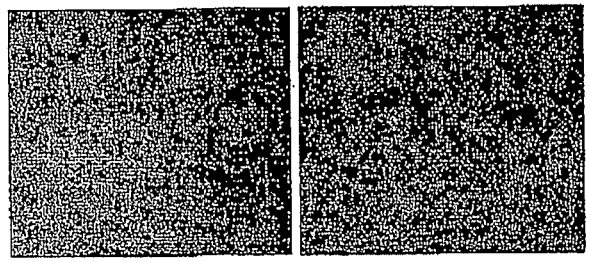
GFP-HUVEC      HEYL-HUVEC
Boyden chamber invasion assay      FIG. 6
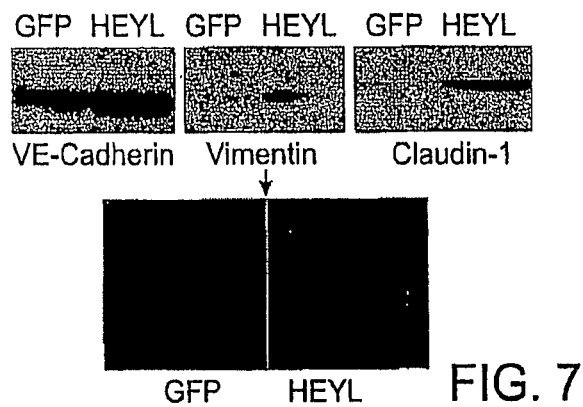
FIG. 7
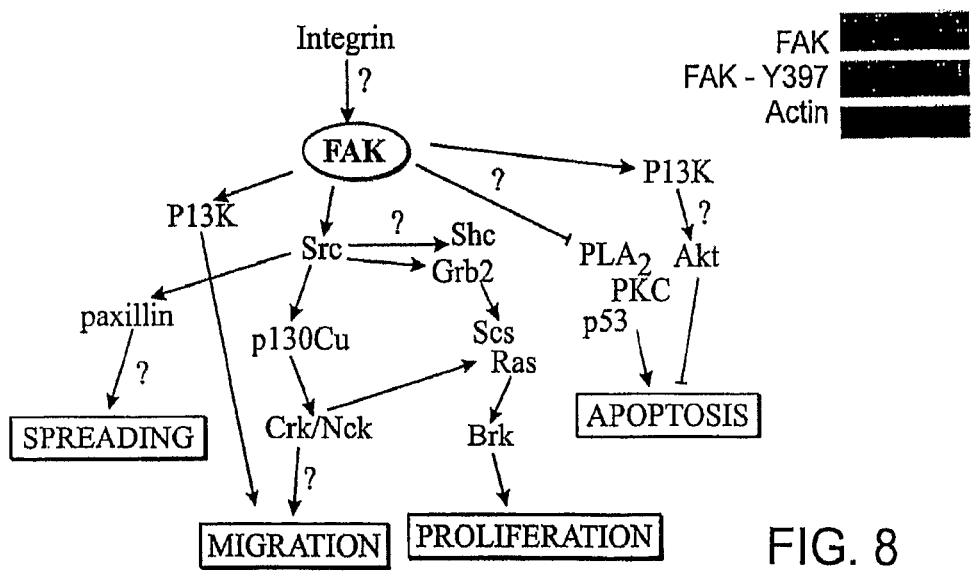
FIG. 8

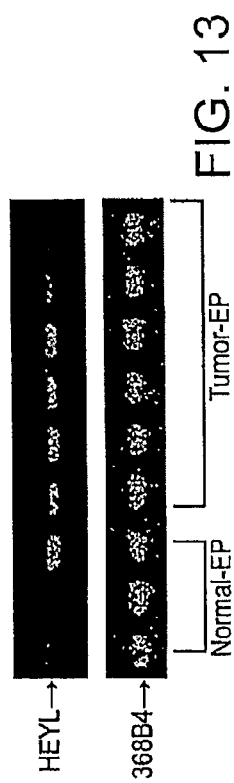
FIG. 13
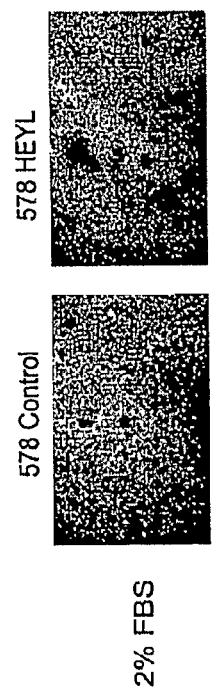
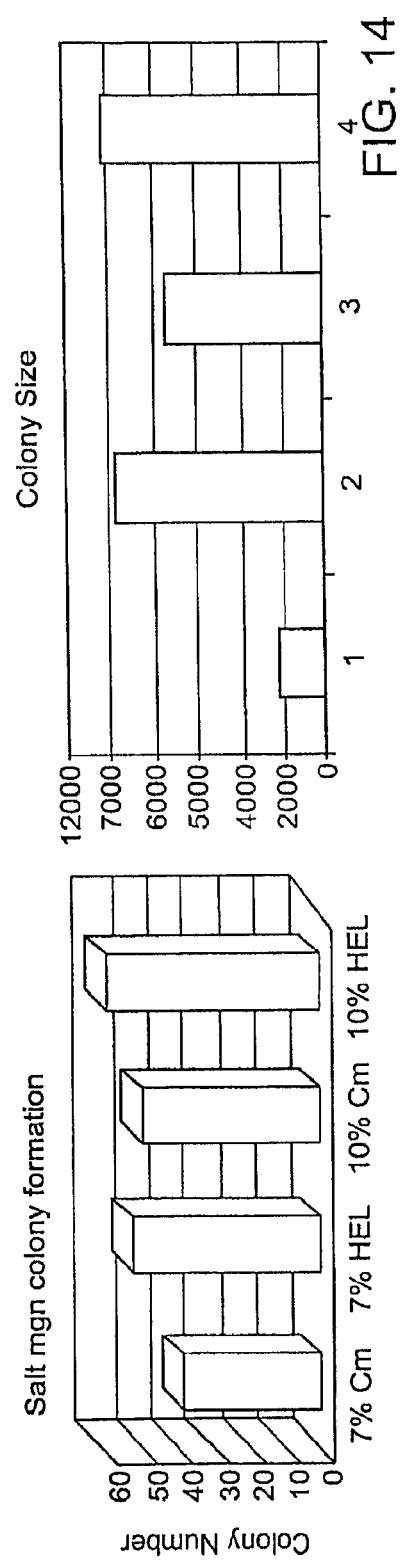
FIG. 14

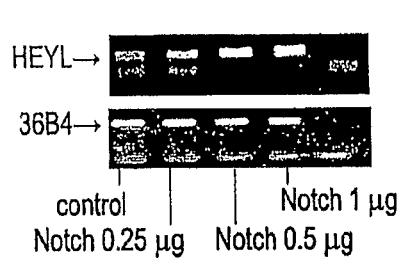 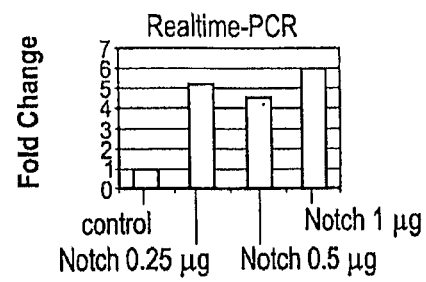
FIG. 22A  FIG. 22B
FIG. 23
FIG. 25

HEYL AS A THERAPEUTIC TARGET AND A DIAGNOSTIC MARKER FOR NEOPLASIA AND USES THEREFOR

CROSS-REFERENCE TO RELATED APPLICATION

This application claims the benefit of the following U.S. Provisional Application No. 60/801,664 which was filed on May 19, 2006, the entire disclosure of which is hereby incorporated in its entirety.

STATEMENT OF RIGHTS TO INVENTIONS MADE UNDER FEDERALLY SPONSORED RESEARCH

This work was supported by a grant from the Department of Defense Breast Cancer Research Program. The government may have certain rights in the invention.

BACKGROUND OF THE INVENTION

Cancer causes one in every four US deaths and is the second leading cause of death among Americans. Among cancers, breast cancer represents the most common form of cancer among women. Each year, more than 180,000 and 1 million women in the U.S. and worldwide, respectively, are diagnosed with breast cancer. Breast cancer is the leading cause of death for women between ages 50-55, and is the most common non-preventable malignancy in women in the Western Hemisphere. It is estimated that 2,167,000 women in the United States are currently living with breast cancer (National Cancer Institute, Surveillance Epidemiology and End Results (NCI SEER) program, Cancer Statistics Review (CSR), on the world wide web at seer.ims.nci.nih.gov/Publications/CSR1973 (1998)). Among women in the United States, breast cancer is the second most common form of cancer, after skin cancer, and ranks second only to lung cancer among causes of cancer deaths in women. Nearly 86% of women who are diagnosed with breast cancer are likely to still be alive five years later, though 24% of them will die of breast cancer after 10 years, and nearly half (47%) will die of breast cancer after 20 years. Moreover, based on cancer rates from 1995 through 1997, a report from the National Cancer Institute (NCI) estimates that about 1 in 8 women in the United States (approximately 12.8 percent) will develop breast cancer during her lifetime (NCI's Surveillance, Epidemiology, and End Results Program (SEER) publication SEER Cancer Statistics Review 1973-1997).

Current therapeutic targets usually aim to inhibit the activity of oncogenes whose expression accounts for a significant number of patients. However, only very few such targets have been identified in breast cancer. Uncovering new therapeutic targets is an ongoing task challenging the breast cancer research community.

Accordingly, improved compositions and methods for the treatment or prevention of neoplasia are required.

SUMMARY OF THE INVENTION

As described below, the present invention features compositions and methods for treating or diagnosing a neoplasia in a subject.

In one aspect, the invention provides a method of diagnosing a subject as having, or having a propensity to develop, a neoplasia, comprising determining the level of expression of a HEYL nucleic acid molecule in a sample, where an increased level of expression relative to a reference, indicates that the subject has or has a propensity to develop a neoplasia.

In another aspect, the invention provides a method of diagnosing a subject as having, or having a propensity to develop, a neoplasia, comprising determining the level of expression of a HEYL polypeptide, or a fragment thereof, in a sample, wherein an increased level of expression relative to the level of expression in a reference, indicates that the subject has or has a propensity to develop a neoplasia.

In one embodiment of the above aspects, the invention further comprises detecting a decrease in the nucleic acid or polypeptide level of Smad3 or a fragment thereof, or any combination thereof in a subject sample.

In another embodiment of the above aspects, the invention further comprises detecting a decrease in TGF-beta activity, or any combination thereof in a subject sample. In a further embodiment, the level of expression is determined in an immunological assay.

In another aspect, the invention features a method of diagnosing a subject as having, or having a propensity to develop, a neoplasia, comprising determining the level of biological activity of a HEYL polypeptide in a subject sample, wherein an alteration in the level of biological activity relative to the biological activity in a reference, indicates that the subject has or has a propensity to develop a neoplasia.

In another aspect, the invention features a method of monitoring a subject diagnosed as having a neoplasia, comprising determining the level of activity of a HEYL polypeptide in a subject sample, wherein an alteration in the level of expression relative to the level of expression in a reference indicates the severity of neoplasia in the subject.

In one particular embodiment, the subject is being treated for a neoplasia.

In another embodiment, the neoplasia is breast cancer, hepatocellular cancer, glioblastoma multiformae, is of stem cell origin, prostate cancer, cervical cancer, lymphoblastic leukemia, ovarian cancer. In a related embodiment, the breast neoplasia is estrogen receptor (+) or estrogen receptor (−).

In one embodiment, the breast neoplasia is selected from primary invasive breast cancer of the ductal or lobular type, metastatic invasive breast cancer ductal carcinoma in situ, atypical ductal hyperplasia.

In a further embodiment, the alteration is an increase, and the increase indicates an increased severity of neoplasia. In another embodiment of any of the above aspects, the reference is a control subject sample. In a particular embodiment, the reference is a subject sample obtained at an earlier time point.

In another embodiment of any of the above aspects, the subject sample is a biological sample.

In another embodiment of any of the above aspects, the method is used to diagnose a subject as having neoplasia.

In another embodiment of any of the above aspects, the method is used to determine the treatment regimen for a subject having neoplasia.

In another embodiment of any of the above aspects, the method is used to monitor the condition of a subject being treated for neoplasia.

In another embodiment of any of the above aspects, the method is used to determine the prognosis of a subject having neoplasia. In a particular embodiment, a poor prognosis determines an aggressive treatment regimen for the subject.

In one aspect, the invention features a method for identifying a subject as having or having a propensity to develop a neoplasia, comprising detecting an alteration in the sequence of a HEYL nucleic acid molecule relative to the sequence or expression of a reference molecule.

In one embodiment, the alteration is detected using a hybridization reaction.

In one aspect, the invention features a HEYL antibody that specifically binds to a HEYL protein or fragment thereof.

In one embodiment, the antibody binds to a HEYL polypeptide. In certain examples, the epitope that the antibody recognizes is EPSGSDGESDGPID (SEQ ID No: 1).

In another aspect, the invention features a polypeptide comprising an isolated HEYL protein, a HEYL variant, or a fragment thereof, wherein the protein or variant or fragment is upregulated in a neoplastic cell.

In one embodiment, the HEYL protein, variant or fragment comprises at least a basic domain, or a helix-loop-helix domain or a combination thereof, and is capable of binding a Smad protein or TGF-beta. In one embodiment, the polypeptide is a fusion protein. In another embodiment the polypeptide is linked to a detectable amino acid sequence. In another embodiment the polypeptide is linked to an affinity tag.

In a further embodiment, the nucleic acid molecule encodes a polypeptide of any one of the above-described aspects.

Another embodiment of the invention is a vector comprising the nucleic acid molecule as described in the above aspects.

In another aspect, the invention features an isolated HEYL inhibitory nucleic acid molecule, wherein the inhibitory nucleic acid molecule specifically binds at least a fragment of a nucleic acid molecule encoding a HEYL protein.

In one embodiment, the vector comprises a nucleic acid molecule encoding the nucleic acid molecule as described in the above-mentioned aspect. In another embodiment, the vector is an expression vector. In one embodiment, the nucleic acid molecule is positioned for expression. In another embodiment, the nucleic acid molecule is operably linked to a promoter. In one embodiment, the promoter is suitable for expression in a mammalian cell.

In a further embodiment, the host cell comprises a nucleic acid molecule of any one of the above-described aspects.

In one embodiment, the cell expresses a HEYL protein variant. In another embodiment, the cell is in vitro. In another embodiment, the cell is in vivo.

In a further embodiment, the cell is a mammalian cell.

In another aspect, the invention features a double-stranded RNA molecule corresponding to at least a portion of a HEYL nucleic acid molecule that encodes a HEYL protein, wherein the double-stranded RNA is capable of altering the level of protein encoded by the HEYL nucleic acid molecule.

In one embodiment, the RNA is an inhibitory RNA. In another embodiment, the RNA is an siRNA.

In another aspect, the invention features an antisense nucleic acid molecule, wherein the antisense nucleic acid molecule is complementary to at least six nucleotides of a HEYL nucleic acid molecule that encodes a HEYL protein, and wherein the antisense is capable of altering expression from the nucleic acid molecule to which it is complementary.

In another aspect, the invention features a primer capable of binding to a HEYL nucleic acid molecule encoding a HEYL protein variant that is upregulated in a neoplastic tissue. In certain embodiments, the sequences of the primers used to determine HEYL overexpression are: Sense (S): CAACTCCTCCTCCTCCTCCT (SEQ ID NO: 2) and antisense (AS): TTGCAACGTGGAAATGTGTT (SEQ ID NO: 3).

In one aspect, the invention features pharmaceutical composition comprising an effective amount of a HEYL protein, variant, or fragment thereof, and a pharmaceutically acceptable excipient, wherein the fragment is capable of modulating cell proliferation or cell cycle.

In one embodiment, the pharmaceutical composition comprises an effective amount of a nucleic acid molecule of any one of the above-mentioned aspects and a pharmaceutically acceptable excipient, wherein the fragment is capable of modulating cell proliferation or cell cycle.

In another embodiment, the composition further inhibits the p15 tumor suppressor.

In a further aspect, the invention features a pharmaceutical composition comprising an effective amount of a vector comprising a nucleic acid molecule encoding a HEYL protein of any one of the above-mentioned aspects in a pharmaceutically acceptable excipient, wherein expression of the HEYL protein in the cell is capable of modulating cell proliferation or cell cycle.

In one aspect, the invention features a HEYL biomarker purified on a biochip.

In one aspect, the invention features a microarray comprising at least two nucleic acid molecules, or fragments thereof, fixed to a solid support, wherein at least one of the nucleic acid molecules is a HEYL nucleic acid molecule.

In another aspect, the invention features a microarray comprising at least two polypeptides, or fragments thereof, bound to a solid support, wherein at least one of the polypeptides on the support is a HEYL polypeptide.

In a further aspect, the invention features a diagnostic kit for the diagnosis of a neoplasia in a subject comprising a HEYL nucleic acid molecule, or fragment thereof, and written instructions for use of the kit for detection of a neoplasia.

In another further aspect, the invention features a diagnostic kit for the diagnosis of a neoplasia in a subject comprising an antibody that specifically binds a HEYL polypeptide, or fragment thereof, and written instructions for use of the kit for detection of a neoplasia.

In another further aspect, the invention features a kit identifying a subject as having or having a propensity to develop a neoplasia, comprising an adsorbent, wherein the adsorbent retains a HEYL biomarker, and written instructions for use of the kit for detection of a neoplasia.

In another further aspect, the invention features a kit comprising a first capture reagent that specifically binds a HEYL biomarker, and written instructions for use of the kit for detection of a neoplasia.

In one embodiment, the kit of any one of the above-mentioned claims is used to detect a neoplasia that is selected from breast cancer, hepatocellular cancer, glioblastoma multiformae, is of stem cell origin, prostate cancer, cervical cancer, lymphoblastic leukemia, ovarian cancer. In another embodiment, the breast neoplasia is estrogen receptor (+) or estrogen receptor (−). In another embodiment, the breast neoplasia is selected from primary invasive breast cancer of the ductal or lobular type, metastatic invasive breast cancer ductal carcinoma in situ, atypical ductal hyperplasia.

In one aspect, the invention teaches a method for detecting neoplasia in a subject sample, the method comprising contacting a subject sample with a capture reagent affixed to a substrate; and then capturing a HEYL polypeptide or nucleic acid molecule with the capture reagent.

In one embodiment the subject sample comprises a HEYL protein or fragment thereof. In another embodiment, the proteins are fractionated prior to contacting the capture reagent.

In another aspect, the invention teaches a method of altering the expression of a HEYL nucleic acid molecule in a cell, the method comprising contacting the cell with an effective amount of a compound capable of altering the expression of a HEYL nucleic acid molecule.

In one embodiment, the compound is a HEYL antisense nucleic acid molecule, a small interfering RNA (siRNA), or a double stranded RNA (dsRNA) that inhibits the expression of a HEYL nucleic acid molecule.

In one aspect, the invention teaches a method of altering HEYL protein expression in a cell, the method comprising contacting the cell with a compound capable of altering the expression of a HEYL polypeptide.

In one embodiment, the cell is a human cell. In another embodiment, the cell is a mammalian cell.

In one embodiment, the cell is a neoplastic cell.

In one embodiment, the cell is in vitro.

In one embodiment, the cell is in vivo.

In another aspect, the invention teaches a method of treating or preventing a neoplasia, comprising administering to a subject an effective amount of a pharmaceutical composition that alters expression of a HEYL polypeptide.

In another aspect, the invention teaches a method of identifying a compound that inhibits a neoplasia, comprising contacting a cell that expresses a HEYL nucleic acid molecule with a candidate compound, and comparing the level of expression of the nucleic acid molecule in the cell contacted by the candidate compound with the level of expression in a control cell not contacted by the candidate compound, wherein an alteration in expression of the HEYL nucleic acid molecule identifies the candidate compound as a compound that inhibits a neoplasia.

In one embodiment, the alteration in expression is a decrease in transcription.

In another embodiment, the alteration in expression is a decrease in translation.

In one aspect, the invention teaches a method of identifying a compound that inhibits a neoplasia, comprising contacting a cell that expresses a HEYL polypeptide with a candidate compound, and comparing the level of expression of the polypeptide in the cell contacted by the candidate compound with the level of polypeptide expression in a control cell not contacted by the candidate compound, wherein an alteration in the expression of the HEYL polypeptide identifies the candidate compound as a compound that inhibits a neoplasia.

In another aspect, the invention teaches a method of identifying a compound that inhibits a neoplasia, comprising contacting a cell that expresses a HEYL polypeptide with a candidate compound, and comparing the biological activity of the polypeptide in the cell contacted by the candidate compound with the level of biological activity in a control cell not contacted by the candidate compound, wherein an alteration in the biological activity of the HEYL polypeptide identifies the candidate compound as a candidate compound that inhibits a neoplasia.

In one embodiment, wherein the cell is in vitro.

In another embodiment, the cell is in vivo.

In one embodiment, the cell is a human cell.

In another embodiment, the cell is a neoplastic cell.

In another embodiment, the alteration in expression is assayed using an immunological assay, an enzymatic assay, or a radioimmunoassay.

In one aspect, the invention teaches a method of identifying a candidate compound that inhibits a neoplasia, comprising contacting a cell containing a HEYL nucleic acid molecule present in an expression vector that includes a reporter construct detecting the level of reporter gene expression in the cell contacted with the candidate compound with a control cell not contacted with the candidate compound, wherein an alteration in the level of the reporter gene expression identifies the candidate compound as a candidate compound that inhibits a neoplasia.

In one embodiment, the neoplasia is breast neoplasia.

Other features and advantages of the invention will be apparent from the detailed description, and from the claims.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant a polypeptide, polynucleotide, or fragment, or analog thereof, small molecule, or other biologically active molecule.

By "alteration" is meant a change (increase or decrease) in the expression levels of a gene or polypeptide as detected by standard art known methods such as those described above. As used herein, an alteration includes a 10% change in expression levels, preferably a 25% change, more preferably a 40% change, and most preferably a 50% or greater change in expression levels.

By "antisense molecule" is meant a non-enzymatic nucleic acid molecule or analog or variant thereof that binds to a target nucleic acid molecule sequence by means of complementary base pairing, such as an RNA-RNA or RNA-DNA interactions and alters the expression of the target sequence. Typically, antisense molecules are complementary to a target sequence along a single contiguous sequence of the antisense molecule. In certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of a target sequence.

By "atypical ductal hyperplasia" is meant a condition that can occur in the lining of the milk ducts in the breast where the duct that has developed extra cells, termed hyperplasia.

The phrase "in combination with" is intended to refer to all forms of administration that provide an inhibitory nucleic acid molecule together with a second agent, such as a second inhibitory nucleic acid molecule or a chemotherapeutic agent, where the two are administered concurrently or sequentially in any order.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "complementary" is meant capable of pairing to form a double-stranded nucleic acid molecule or portion thereof. In one embodiment, an antisense molecule is in large part complementary to a target sequence. The complementarity need not be perfect, but may include mismatches at 1, 2, 3, or more nucleotides.

By "control" is meant a standard or reference condition.

By "corresponds" is meant comprising at least a fragment of a double-stranded gene, such that a strand of the double-stranded inhibitory nucleic acid molecule is capable of binding to a complementary strand of the gene.

By "decreases" is meant a reduction by at least about 5% relative to a reference level. A decrease may be by 5%, 10%, 15%, 20%, 25% or 50%, or even by as much as 75%, 85%, 95% or more.

By "an effective amount" is meant the amount of an agent required to ameliorate the symptoms of a disease relative to an untreated patient. The effective amount of active agent(s) used to practice the present invention for therapeutic treatment of a neoplasia varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion (e.g., at least 10, 25, 50, 100, 125, 150, 200, 250, 300, 350, 400, or 500 amino acids or nucleic acids) of a protein or nucleic acid molecule that is substantially identical to a reference protein or nucleic acid and retains the biological activity of the reference A "host cell" is any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

By "inhibits a neoplasia" is meant decreases the propensity of a cell to develop into a neoplasia or slows, decreases, or stabilizes the growth or proliferation of a neoplasia.

By "inhibitory nucleic acid molecule" is meant a single stranded or double-stranded RNA, siRNA (short interfering RNA), shRNA (short hairpin RNA), or antisense RNA, or a portion thereof, or an analog or mimetic thereof, that when administered to a mammalian cell results in a decrease (e.g., by 10%, 25%, 50%, 75%, or even 90-100%) in the expression of a target sequence. Typically, a nucleic acid inhibitor comprises or corresponds to at least a portion of a target nucleic acid molecule, or an ortholog thereof, or comprises at least a portion of the complementary strand of a target nucleic acid molecule.

By "marker" is meant any protein or polynucleotide having an alteration in expression level or activity that is associated with a disease or disorder.

The term "microarray" is meant to include a collection of nucleic acid molecules or polypeptides from one or more organisms arranged on a solid support (for example, a chip, plate, or bead).

By "neoplasia" is meant any disease that is caused by or results in inappropriately high levels of cell division, inappropriately low levels of apoptosis, or both. For example, cancer is a neoplasia. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinooma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

By "nucleic acid" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced stability in the presence of nucleases.

By "obtaining" as in "obtaining the inhibitory nucleic acid molecule" is meant synthesizing, purchasing, or otherwise acquiring the inhibitory nucleic acid molecule.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

By "positioned for expression" is meant that the polynucleotide of the invention (e.g., a DNA molecule) is positioned adjacent to a DNA sequence that directs transcription and translation of the sequence (i.e., facilitates the production of, for example, a recombinant microRNA molecule described herein).

By "portion" is meant a fragment of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 5, 6, 7, 8, 9, 10, 11, 12, 13, 14, 15, 16, 17, 18, 19, 20, or 21 nucleotides.

By "reference" is meant a standard or control condition.

By "reporter gene" is meant a gene encoding a polypeptide whose expression may be assayed; such polypeptides include, without limitation, glucuronidase (GUS), luciferase, chloramphenicol transacetylase (CAT), and beta-galactosidase.

The term "siRNA" refers to small interfering RNA; a siRNA is a double stranded RNA that "corresponds" to or matches a reference or target gene sequence. This matching need not be perfect so long as each strand of the siRNA is capable of binding to at least a portion of the target sequence. SiRNA can be used to inhibit gene expression, see for example Bass, 2001, Nature, 411, 428 429; Elbashir et al., 2001, Nature, 411, 494 498; and Zamore et al., Cell 101:25-33 (2000).

The term "subject" is intended to include vertebrates, preferably a mammal. Mammals include, but are not limited to, humans.

The term "pharmaceutically-acceptable excipient" as used herein means one or more compatible solid or liquid filler, diluents or encapsulating substances that are suitable for administration into a human.

By "specifically binds" is meant a molecule (e.g., peptide, polynucleotide) that recognizes and binds a protein or nucleic acid molecule of the invention, but which does not substantially recognize and bind other molecules in a sample, for example, a biological sample, which naturally includes a protein of the invention.

By "substantially identical" is meant a protein or nucleic acid molecule exhibiting at least 50% identity to a reference amino acid sequence (for example, any one of the amino acid sequences described herein) or nucleic acid sequences (for example, any one of the nucleic acid sequences described herein). Preferably, such a sequence is at least 60%, more preferably 80% or 85%, and still more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "targets" is meant alters the biological activity of a target polypeptide or nucleic acid molecule.

By "transformed cell" is meant a cell into which (or into an ancestor of which) has been introduced, by means of recombinant DNA techniques, a polynucleotide molecule encoding (as used herein) a protein of the invention.

By "vector" is meant a nucleic acid molecule, for example, a plasmid, cosmid, or bacteriophage, that is capable of replication in a host cell. In one embodiment, a vector is an expression vector that is a nucleic acid construct, generated recombinantly or synthetically, bearing a series of specified nucleic acid elements that enable transcription of a nucleic acid molecule in a host cell. Typically, expression is placed under the control of certain regulatory elements, including constitutive or inducible promoters, tissue-preferred regulatory elements, and enhancers.

BRIEF DESCRIPTION OF THE DRAWINGS

FIG. 1 shows a structural comparison of HES, HEYL and related family members.

FIG. 6 shows HEYL-HUVEC cells invade more efficiently through Matrigel.

FIG. 7 shows upregulation of adhesion molecule and fibroblast cytoskeleton in HEYL-HUVEC cells. The top panels show western blotting for VE-cadherin (left panels), Vimentin (middle panels) and Claudin (right panels). The bottom panels show Vimentin staining.

FIGS. 8A and 8B show possible signaling mechanisms. Focal Adhesion Kinase, or FAK, is a protein tyrosine kinase. FAK discretely localizes within cells to focal adhesions, regions where the cell comes in close contact with the extracellular matrix. FAK is a major component of a signaling pathway that is controlled by integrins, which are receptors for proteins in the extracellular matrix. Other stimuli, like growth factors, can also stimulate FAK activity and FAK may play an important role in cross talk between the integrins and growth factor receptors. Cell motility and cell survival are two important biological processes that are controlled by FAK. Since cancerous/metastatic cells exhibit altered cell motility and survival, altered FAK signaling, known to act through activating PI3K and src signaling and block PLA2, may promote some of the phenotypes exhibited in cancer cells, like proliferation, migration and invasion. B HEYL-HUVEC cells show upregulation of FAK and its phosphorylated form.

FIG. 13 shows that microdissected epithelial cells express HEYL mRNA.

FIG. 14 shows the results of a HG578T soft agar assay for anchorage independent growth.

FIGS. 22 A and 22 B shows transient expression of Notch1 results in HEYL mRNA upregulation.

FIG. 23 shows HEYL transformed NIH3T3 cells grow in nude mice.

FIG. 25 is a photo of nude mice showing that HEYL expression promotes cell growth in vivo.

DETAILED DESCRIPTION OF THE INVENTION

Figure 1A:
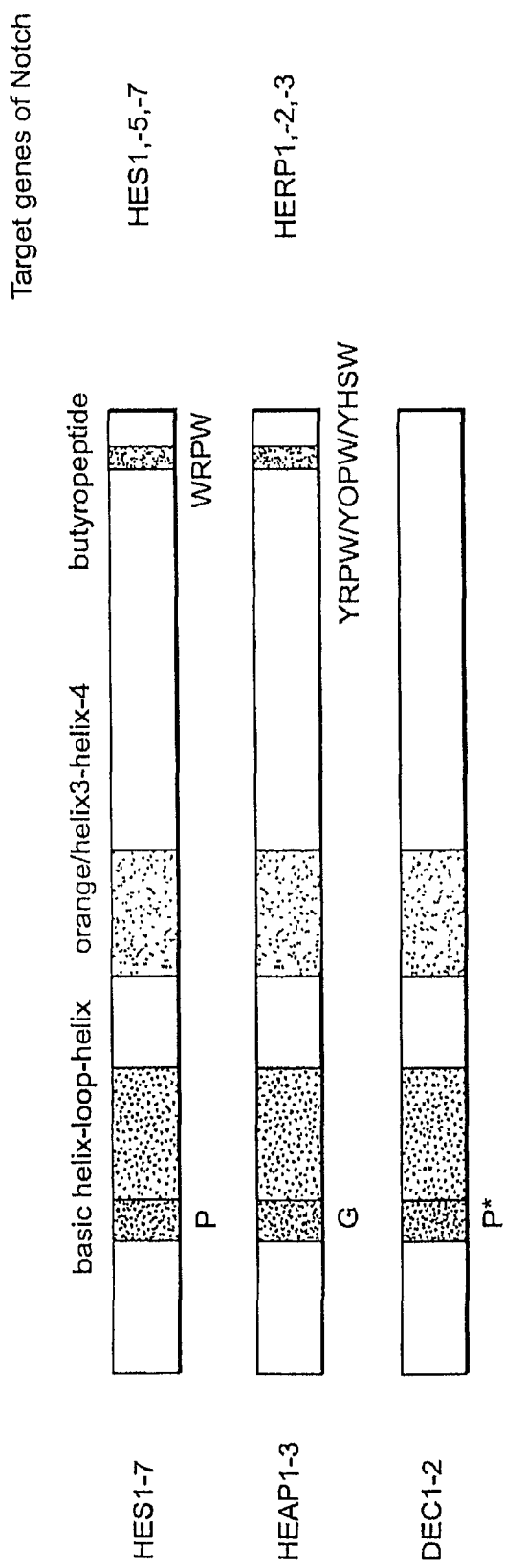
FIG. 1A discloses SEQ ID NOS 4-7, respectively, in order of appearance.

Described here is the identification of a new oncogene, HEYL, in cancer, and in particular breast cancer. HEYL was found to be overexpressed at high frequency in patients from the very early stages of breast cancer development to the late metastasis phase. HEYL transcriptionally targets the cell cycle inhibitor, p 15, reducing its effect and allowing cells to progress through the cell cycle faster. HEYL is a downstream effector of the Notch pathway that has been found to be involved in breast cancer. The function of HEYL is to increase cancer cell proliferation and possibly to antagonize the cytostatic effect of TGF-beta signal transduction pathway, and thus this gene plays a significant role in facilitating breast cancer development. Due to its high frequency in breast cancer patients and persistent expression during the entire course of cancer development, HEYL represents a new therapeutic target.

The invention generally features compositions and methods that are useful for treating or diagnosing a neoplasia. The invention is based in part on the observation that increased HEYL expression was found in breast cancer tissue. Accordingly, the invention provides methods of diagnosing a subject as having a neoplasia based on increased HEYL expression. The invention further provides compositions and methods for altering the expression of HEYL and thereby treating a neoplasia.

HEYL

Hey proteins, also known as Hesr, Hit, Chf, Herp, and gridlock, have been shown to regulate a variety of cellular decisions in different processes such as cardiac development, angiogenesis, neurogenesis, gliogenesis, bone development, or the epithelial-to-mesenchymal transition (EMT). Besides their role in physiological developmental processes, Hey genes have also been implicated as possible tumor suppressors (20).

Inhibitory Nucleic Acid Molecules

Given that increased levels of HEYL are associated with cancer, and in certain embodiments breast cancer, the invention provides compositions that inhibit the expression of HEYL, as well as methods of using such compositions for the treatment of cancer. In one embodiment, the invention provides inhibitory nucleic acid molecules, such as antisense nucleic acid molecules, that decrease the expression of HEYL. Inhibitory nucleic acid molecules are essentially nucleobase oligomers that may be employed to decrease the expression of a target nucleic acid sequence, such as a nucleic acid sequence that encodes HEYL. The inhibitory nucleic acid molecules provided by the invention include any nucleic acid molecule sufficient to decrease the expression of a HEYL nucleic acid molecule by at least 5-10%, desirably by at least 25%-50%, or even by as much as 75%-100%. Each of the nucleic acid sequences provided herein may be used, for example, in the discovery and development of therapeutic antisense nucleic acid molecules to decrease the expression of a HEYL. If desired, one or more antisense nucleic acid molecules to HEYL are administered in combination, for example an antisense molecule to the basic domain, or an antisense molecule to the helix loop helix domain, such that the coordinated reduction in expression is achieved. Other advantageous regions to target may be regions that interact with the promoter region of a target gene or the repressor region of a target gene, or interaction with a transcriptional regulator, for example a transcriptional co-activator. For example, but not limited to, regions of Notch ICD that interact with CSL enhancer protein(s).

Further, the invention provides inhibitory nucleic acid molecules, such as antisense nucleic acid molecules, that decrease the expression of Smad3 or inhibitory nucleic acid molecules, such as antisense nucleic acid molecules that decrease expression of Notch or Notch ICD, for example, but not limited to, Notch 1, Notch 2, Notch 3 or Notch 4. It was found that HEYL could interact with Smad3. It was also found that increasing the amount of Notch 1 intracellular domain (ICD) increased HEYL activity in an assay for luciferase activity. Thus, the inhibitory nucleic acid molecules provided by the invention include any nucleic acid molecule sufficient to decrease the expression of a Smad3 nucleic acid molecule or Notch (e.g. Notch 1, Notch 2, Notch 3, or Notch 4) or Notch ICD, by at least 5-10%, desirably by at least 25%-50%, or even by as much as 75%-100%. Each of the nucleic acid sequences provided herein may be used, for example, in the discovery and development of therapeutic antisense nucleic acid molecules to decrease the expression of Smad3 or Notch ligand (e.g. Notch 1, Notch 2, Notch 3, or Notch 4). If desired, one or more antisense nucleic acid molecules to Smad3 or Notch (e.g. Notch 1, Notch 2, Notch 3, or Notch 4) or Notch ICD are administered in combination with antisense nucleic acid molecules to HEYL, such that the coordinated reduction in expression is achieved.

The invention is not limited to antisense nucleic acid molecules but encompasses virtually any single-stranded or double-stranded nucleic acid molecule that decreases expression of HEYL, Notch ligand (for example, but not limited to, Notch (e.g. Notch 1, Notch 2, Notch 3, or Notch 4) or Notch ICD, or Smad3. Thus, the invention further provides catalytic RNA molecules or ribozymes. Such catalytic RNA molecules can be used to inhibit expression of a HEYL or a Notch or Notch ICD or Smad 3 nucleic acid molecule in vivo.

The inclusion of ribozyme sequences within an antisense RNA confers RNA-cleaving activity upon the molecule, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference. In various embodiments of this invention, the catalytic nucleic acid molecule is formed in a hammerhead or hairpin motif. Examples of such hammerhead motifs are described by Rossi et al., Nucleic Acids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

In another approach, the inhibitory nucleic acid molecule is a double-stranded nucleic acid molecule used for RNA interference (RNAi)-mediated knock-down of the expression of HEYL, Notch or Notch ICD or Smad3. siRNAs are also useful for the inhibition of HEYL, Notch or Notch ICD or Smad3. See, for example, Nakamoto et al., Hum Mol Genet, 2005. Desirably, the siRNA is designed such that it provides for the cleavage of a target microRNA of the invention. In one embodiment, a double-stranded RNA (dsRNA) molecule is made that includes between eight and twenty-five (e.g., 8, 10, 12, 15, 16, 17, 18, 19, 20, 21, 22, 23, 24, 25) consecutive nucleobases of a nucleobase oligomer of the invention. The dsRNA can be two complementary strands of RNA that have duplexed, or a single RNA strand that has self-duplexed (small hairpin (sh) RNA). Typically, dsRNAs are about 21 or 22 base pairs, but may be shorter or longer (up to about 29 nucleobases) if desired. Double stranded RNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference. An inhibitory nucleic acid molecule that "corresponds" to HEYL, Notch or Notch ICD or Smad3 comprises at least a fragment of the double-stranded gene, such that each strand of the double-stranded inhibitory nucleic acid molecule is capable of binding to the complementary strand of the target gene. The inhibitory nucleic acid molecule need not have perfect correspondence or need not be perfectly complementary to the reference sequence. In one embodiment, an siRNA has at least about 85%, 90%, 95%, 96%, 97%, 98%, or even 99% sequence identity with the target nucleic acid. For example, a 19 base pair duplex having 1-2 base pair mismatch is considered useful in the methods of the invention. In other embodiments, the nucleobase sequence of the inhibitory nucleic acid molecule exhibits 1, 2, 3, 4, 5 or more mismatches.

Inhibitory nucleic acid molecules of the invention also include double stranded nucleic acid "decoys." Decoy molecules contain a binding site for a transcription factor that is responsible for the deregulated transcription of a gene of interest. The present invention provides decoys that competitively block binding to a regulatory element in a target gene e.g., the region in HEYL that binds the ICD portion of Notch, for example the ICD of Notch1. One of skill in the art understands that the examples are not limited to Notch 1, but can also include any of the Notch proteins, for example Notch 1, 2, 3, or 4. The competitive inhibition of Notch ICD binding by the decoy results in the indirect inhibition of transcription of HEYL target. An overview of decoy technology is provided by Suda et al., Endocr. Rev., 1999, 20, 345-357; S. Yla-Herttuala and J. F. Martin, The Lancet 355, 213-222, 2000). In one therapeutic method, short double-stranded DNA decoy molecules are introduced into cells (e.g., neoplastic cells) of a subject. The decoys are provided in a form that facilitates their entry into target cells of the subject. Having entered a cell, the decoy specifically binds an endogenous transcription factor, for example HEYL, thereby competitively inhibiting the transcription factor from binding to an endogenous gene. The decoys are administered in amounts and under conditions whereby binding of the endogenous transcription factor to the endogenous gene is effectively competitively inhibited without significant host toxicity. Depending on the transcription factor, the methods can effect up- or down-regulation of gene expression. The subject compositions comprise the decoy molecules in a context that provides for pharmacokinetics sufficient for effective therapeutic use.

In one embodiment, the inhibitory nucleic acid molecules of the invention are administered systemically in dosages between about 1 and 100 mg/kg (e.g., 1, 5, 10, 20, 25, 50, 75, and 100 mg/kg). In other embodiments, the dosage ranges from between about 25 and 500 mg/m$^2$/day. Desirably, a human patient having a neoplasia receives a dosage between about 50 and 300 mg/m$^2$/day (e.g., 50, 75, 100, 125, 150, 175, 200, 250, 275, and 300).

HEYL Polynucleotides

In general, the invention includes any nucleic acid sequence encoding HEYL of the as well as nucleic acid molecules containing at least one strand that hybridizes with a nucleic acid sequence of HEYL (e.g., an inhibitory nucleic acid molecule, such as an antisense molecule, a dsRNA, siRNA, or shRNA). The inhibitory nucleic acid molecules of the invention can be between 8-200 nucleotides in length. In some embodiments, the inhibitory nucleic acid molecules of the invention comprises 8, 10, 15, 16, 17, 18, 19, 20, 21, 22, 23, 24, 25, 26, 27, 28, 29, 30, 31, 32, 33, 34, 35, 45, or complementary nucleotide residues. In yet other embodiments, the antisense molecules are 60%, 65%, 70%, 75%, 80%, 85%, 90%, 95%, 96%, 97%, 98%, 99% complementary to the target sequence. An isolated nucleic acid molecule can be manipulated using recombinant DNA techniques well known in the art. Thus, a nucleotide sequence contained in a vector in which 5' and 3' restriction sites are known, or for which polymerase chain reaction (PCR) primer sequences have been disclosed, is considered isolated, but a nucleic acid sequence existing in its native state in its natural host is not. An isolated nucleic acid may be substantially purified, but need not be. For example, a nucleic acid molecule that is isolated within a cloning or expression vector may comprise only a tiny percentage of the material in the cell in which it resides. Such a nucleic acid is isolated, however, as the term is used herein, because it can be manipulated using standard techniques known to those of ordinary skill in the art.

Also included in the invention are HEYL polypeptides, variants, or fragments thereof containing at least one alteration relative to a reference sequence. Such alterations include certain mutations, deletions, insertions, or post-translational modifications. The invention further includes analogs of any naturally-occurring polypeptide of the invention. Analogs can differ from naturally-occurring polypeptides of the invention by amino acid sequence differences, by post-translational modifications, or by both. Analogs of the invention will generally exhibit at least 85%, more preferably 90%, and most preferably 95% or even 99% identity with all or part of a naturally-occurring amino acid sequence of the invention. The length of sequence comparison is at least 10, 13, 15 amino acid residues, preferably at least 25 amino acid residues, and more preferably more than 35 amino acid residues. To determine the degree of identity, a BLAST program may be used, with a probability score between e-3 and e-100 indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Mullets, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids.

In addition to full-length polypeptides, the invention also includes fragments of any one of the polypeptides of the invention. As used herein, the term "a fragment" means at least 5, 10, 13, or 15 amino acids. In other embodiments a fragment is at least 20 contiguous amino acids, at least 30 contiguous amino acids, or at least 50 contiguous amino acids, and in other embodiments at least 60 to 80 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Delivery of Nucleobase Oligomers

Naked oligonucleotides are capable of entering tumor cells and inhibiting the expression of HEYL. Nonetheless, it may be desirable to utilize a formulation that aids in the delivery of an inhibitory nucleic acid molecule or other nucleobase oligomers to cells (see, e.g., U.S. Pat. Nos. 5,656,611, 5,753,613, 5,785,992, 6,120,798, 6,221,959, 6,346,613, and 6,353,055, each of which is hereby incorporated by reference).

Polynucleotide Therapy

Polynucleotide therapy featuring a polynucleotide encoding an inhibitory nucleic acid molecule or analog thereof that targets HEYL is another therapeutic approach for treating a neoplasia in a subject. Expression vectors encoding inhibitory nucleic acid molecules can be delivered to cells of a subject having a neoplasia. The nucleic acid molecules must be delivered to the cells of a subject in a form in which they can be taken up and are advantageously expressed so that therapeutically effective levels can be achieved.

Methods for delivery of the polynucleotides to the cell according to the invention include using a delivery system such as liposomes, polymers, microspheres, gene therapy vectors, and naked DNA vectors.

Transducing viral (e.g., retroviral, adenoviral, lentiviral and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding an inhibitory nucleic acid molecule can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77 S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for the introduction of an inhibitory nucleic acid molecule therapeutic to a cell of a patient diagnosed as having a neoplasia. For example, an inhibitory nucleic acid molecule that targets HEYL can be introduced into a cell by administering the nucleic acid in the presence of a lipofection agent (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Preferably the inhibitory nucleic acid molecules are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell.

Inhibitory nucleic acid molecule expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers.

For any particular subject, the specific dosage regimes should be adjusted over time according to the individual need and the professional judgment of the person administering or supervising the administration of the compositions.

Pharmaceutical Compositions

As reported herein, an increase in the expression of HEYL is associated with cancer. Accordingly, the invention provides therapeutic compositions that decrease the expression of HEYL to treat neoplasia. In one embodiment, the present invention provides a pharmaceutical composition comprising an inhibitory nucleic acid molecule (e.g., an antisense, siRNA, or shRNA polynucleotide) that decreases the expression of one or more nucleic acid molecules encoded by HEYL. The invention also provides inhibitory nucleic acid molecules that decrease the expression of one or more nucleic acid molecules encoded by Smad3 or Notch (e.g. Notch 1, 2, 3, or 4). If desired, the inhibitory nucleic acid molecule is administered in combination with a chemotherapeutic agent. Polynucleotides of the invention may be administered as part of a pharmaceutical composition. The compositions should be sterile and contain a therapeutically effective amount of the polypeptides or nucleic acid molecules in a unit of weight or volume suitable for administration to a subject.

An inhibitory nucleic acid molecule of the invention may be administered within a pharmaceutically acceptable diluent, carrier, or excipient, in unit dosage form. Conventional pharmaceutical practice may be employed to provide suitable formulations or compositions to administer the compounds to patients suffering from a neoplasia (e.g., cancer). Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for inhibitory nucleic acid molecules include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a neoplastic disease or condition. The preferred dosage of a nucleobase oligomer of the invention is likely to depend on such variables as the type and extent of the disorder, the overall health status of the particular patient, the formulation of the compound excipients, and its route of administration.

With respect to a subject having a neoplastic disease or disorder, an effective amount is sufficient to stabilize, slow, or reduce the proliferation of the neoplasm. Generally, doses of active polynucleotide compositions of the present invention would be from about 0.01 mg/kg per day to about 1000 mg/kg per day. It is expected that doses ranging from about 50 to about 2000 mg/kg will be suitable. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of an antisense targeting HEYL, Smad3 or Notch.

A variety of administration routes are available. The methods of the invention, generally speaking, may be practiced using any mode of administration that is medically acceptable, meaning any mode that produces effective levels of the active compounds without causing clinically unacceptable adverse effects. Other modes of administration include oral, rectal, topical, intraocular, buccal, intravaginal, intracisternal, intracerebroventricular, intratracheal, nasal, transdermal, within/on implants, e.g., fibers such as collagen, osmotic pumps, or grafts comprising appropriately transformed cells, etc., or parenteral mutes.

Therapy

Therapy may be provided wherever cancer therapy is performed: at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of cancer being treated, the age and condition of the patient, the stage and type of the patient's disease, and how the patient's body responds to the treatment. Drug administration may be performed at different intervals (e.g., daily, weekly, or monthly). Therapy may be given in on-and-off cycles that include rest periods so that the patient's body has a chance to build healthy new cells and regain its strength.

Depending on the type of cancer and its stage of development, the therapy can be used to slow the spreading of the cancer, to slow the cancer's growth, to kill or arrest cancer cells that may have spread to other parts of the body from the original tumor, to relieve symptoms caused by the cancer, or to prevent cancer in the first place. As described above, if desired, treatment with an inhibitory nucleic acid molecule of the invention may be combined with therapies for the treatment of proliferative disease (e.g., radiotherapy, surgery, or chemotherapy). For any of the methods of application described above, an inhibitory nucleic acid molecule of the invention is desirably administered intravenously or is applied to the site of neoplasia (e.g., by injection).

Diagnostics

As described in more detail below, the present invention has identified increases in the expression of HEYL, and corresponding increases in the expression Notch, in particular the intracellular domain of Notch 1, and an interaction between HEYL and Smad3, that are associated with cancer. Thus, alterations in the expression level of one or more (e.g., 1, 2, 3, 4, 5, 6, 7, 8, or 9) of the following markers is used to diagnose a neoplasia: HEYL, Notch ICD, Notch 1 ICD, Smad3. If desired, alterations in the expression of all of these markers is used to diagnose or characterize a neoplasia.

In one embodiment, a subject is diagnosed as having or having a propensity to develop a neoplasia, the method comprising measuring markers in a biological sample from a patient, and detecting an alteration in the expression of test marker molecules relative to the sequence or expression of a reference molecule. The marker is typically HEYL. While the following approaches describe diagnostic methods featuring HEYL, Notch 1 ICD, Smad3, the skilled artisan will appreciate that any one or more of the markers set forth above is useful in such diagnostic methods.

Increased expression of HEYL and/or Notch1 ICD is correlated with neoplasia. Accordingly, the invention provides compositions and methods for identifying a neoplasia in a subject. The present invention provides a number of diagnostic assays that are useful for the identification or characterization of a neoplasia. Alterations in gene expression are detected using methods known to the skilled artisan and described herein. Such information can be used to diagnose a neoplasia.

In one approach, diagnostic methods of the invention are used to assay the expression of HEYL and/or Notch' ICD in a biological sample relative to a reference (e.g., the level of HEYL and/or Notch1 ICD present in a corresponding control tissue). In one embodiment, the level of HEYL and/or Notch1 ICD is detected using a nucleic acid probe that specifically binds HEYL and/or Notch1 ICD. Exemplary nucleic acid probes that specifically bind HEYL and/or Notch1 ICD are described herein. By "nucleic acid probe" is meant any nucleic acid molecule, or fragment thereof, that binds HEYL and/or Notch1 ICD. Such nucleic acid probes are useful for the diagnosis of a neoplasia.

In one approach, quantitative PCR methods are used to identify an increase in the expression of HEYL and/or Notch1 ICD. In another approach, PCR methods are used to identify an alteration in the sequence of HEYL and/or Notch1 ICD. The invention provides probes that are capable of detecting HEYL and/or Notch1 ICD. Such probes may be used to hybridize to a nucleic acid sequence derived from a patient having a neoplasia. The specificity of the probe determines whether the probe hybridizes to a naturally occurring sequence, allelic variants, or other related sequences. Hybridization techniques may be used to identify mutations indicative of a neoplasia or may be used to monitor expression levels of these genes (for example, by Northern analysis (Ausubel et al., supra).

In general, the measurement of a nucleic acid molecule in a subject sample is compared with a diagnostic amount present in a reference. A diagnostic amount distinguishes between a neoplastic tissue and a control tissue. The skilled artisan appreciates that the particular diagnostic amount used can be adjusted to increase sensitivity or specificity of the diagnostic assay depending on the preference of the diagnostician. In general, any significant increase or decrease (e.g., at least about 10%, 15%, 30%, 50%, 60%, 75%, 80%, or 90%) in the level of test nucleic acid molecule or polypeptide in the subject sample relative to a reference may be used to diagnose a neoplasia. Test molecules include any one or more of HEYL, Notch1 ICD, Notch 2 ICD, Notch 3 ICD, Notch 4 ICD, and Smad3. In one embodiment, the reference is the level of test polypeptide or nucleic acid molecule present in a control sample obtained from a patient that does not have aneoplasia. In another embodiment, the reference is a baseline level of test molecule present in a biologic sample derived from a patient prior to, during, or after treatment for a neoplasia. In yet another embodiment, the reference can be a standardized curve.

Antibodies

Antibodies are well known to those of ordinary skill in the science of immunology. As used herein, the term "antibody" means not only intact antibody molecules, but also fragments of antibody molecules that retain immunogen binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments which lack the Fc fragment of intact antibody, clear more rapidly from the circulation, and may have less non specific tissue binding of an intact antibody (Wahl et al., J. Nucl. Med. 24:316 325 (1983). The antibodies of the invention comprise whole native antibodies, bispecific antibodies; chimeric antibodies; Fab, Fab', single chain V region fragments (scFv) and fusion polypeptides.

Included in the invention are HEYL antibodies that specifically bind to a HEYL protein or fragment thereof. In one embodiment, the antibody binds to a HEYL polypeptide. In certain examples, the epitope that the antibody recognizes is EPSGSDGESDGPID (SEQ ID NO: 1).

In certain examples, an antibody that binds a HEYL polypeptide is monoclonal. Alternatively, the anti-HEYL antibody is a polyclonal antibody. The preparation and use of polyclonal antibodies are also known the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F (ab¢) 2" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab¢ fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing a HEYL polypeptides, or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding a HEYL polypeptide, or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding a HEYL polypeptide, or immunogenic fragments thereof, can be expressed in cells in vitro, followed by isolation of the receptor and administration of the receptor to a suitable host in which antibodies are raised.

Using either approach, antibodies can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition; e.g., Pristane. Monoclonal antibodies (Nabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

Types of Biological Samples

The level of markers in a biological sample from a patient having, or at risk for developing a neoplasia can be measured, and an alteration in the expression of test marker molecule relative to the sequence or expression of a reference molecule, can be determined in different types of biologic samples. Test markers include any one or all of the following: HEYL, Notch1 ICD, Notch 2 ICD, Notch 3 ICD, Notch 4 ICD, and Smad3. The biological samples are generally derived from a patient, generally as a tissue sample (e.g. a tissue sample obtained by biopsy).

In certain preferred embodiments, the biological sample is taken from a patient having, or at risk for developing a breast neoplasia. Breast cancer evolves through a series of stages of increasingly abnormal breast ductal cells. As such, breast neoplasia can be defined as pre-malignant or malignant neoplasia. Most types of invasive breast cancer are thought to evolve over long periods from preexisting benign lesions. Of the many types of benign entities found in the human breast, only a few have clinically significant premalignant potential. Currently, among the most well characterized premalignant lesions are atypical ductal hyperplasia, atypical lobular hyperplasia, and lobular carcinoma in situ. Ductal carcinoma in situ (DCIS) is considered to be a preinvasive malignant lesion. Breast cancer is divided into stages as follows. Stage I. In stage I, the tumor is 2 centimeters or smaller and has not spread outside the breast. Stage IIA. In stage IIA: no tumor is found in the breast, but cancer is found in the axillary lymph nodes (the lymph nodes under the arm); or the tumor is 2 centimeters or smaller and has spread to the axillary lymph nodes; or the tumor is larger than 2 centimeters but not larger than 5 centimeters and has not spread to the axillary lymph nodes. Stage IIB. In stage IIB, the tumor is either: larger than 2 centimeters but not larger than 5 centimeters and has spread to the axillary lymph nodes; or larger than 5 centimeters but has not spread to the axillary lymph nodes. Stage IIIA. In stage IIIA: no tumor is found in the breast, but cancer is found in axillary lymph nodes that are attached to each other or to other structures; or the tumor is 5 centimeters or smaller and has spread to axillary lymph nodes that are attached to each other or to other structures; or the tumor is larger than 5 centimeters and has spread to axillary lymph nodes that may be attached to each other or to other structures. Stage IIIB. In stage IIIB, the cancer may be any size and: has spread to tissues near the breast (the skin or chest wall, including the ribs and muscles in the chest); and may have spread to lymph nodes within the breast or under the arm. Stage IIIC. In stage IIIC, the cancer has spread to lymph nodes beneath the collarbone and near the neck; and may have spread to lymph nodes within the breast or under the arm and to tissues near the breast. Stage IIIC breast cancer is divided into operable and inoperable stage IIIC. In operable stage LUC, the cancer: is found in 10 or more of the lymph nodes under the arm; or is found in the lymph nodes beneath the collarbone and near the neck on the same side of the body as the breast with cancer, or is found in lymph nodes within the breast itself and in lymph nodes under the arm. In inoperable stage IIIC breast cancer, the cancer has spread to the lymph nodes above the collarbone and near the neck on the same side of the body as the breast with cancer. Stage IV. In stage IV, the cancer has spread to other organs of the body, most often the bones, lungs, liver, or brain. Any of the tissue described herein is suitable for use as a biological sample in the methods of the invention as described.

It was found in the experiments described herein that HEYL expression correlated with different prognosis in ER-positive and ER-negative patients, therefore samples for use in the methods of the invention as described herein advantageously will be taken from both ER-positive and ER-negative breast tissue. Moreover, effects of test therapeutics, identification of test compounds and other methods will be dependent upon ER receptor status of the tissue sample.

Patient Monitoring

The disease state or treatment of a patient having a neoplasia, for example a breast neoplasia as described herein, can be monitored using the methods and compositions of the invention. In one embodiment, the disease state of a patient can be monitored using the methods and compositions of the invention. Such monitoring may be useful, for example, in assessing the efficacy of a particular drug in a patient. Therapeutics that alter the expression of any one or more of the Markers of the invention (e.g., HEYL, Notch1 ICD, Notch 2 ICD, Notch 3 ICD, Notch 4 ICD, and Smad3) are taken as particularly useful in the invention.

Screening Assays

One embodiment of the invention encompasses a method of identifying an agent that inhibits the expression or activity of HEYL. Accordingly, compounds that modulate the expression or activity of a HEYL nucleic acid molecule, variant, or portion thereof are useful in the methods of the invention for the treatment or prevention of a neoplasm (e.g., breast, colon, lymph, ovary, stomach, thyroid, testis, and uterine cancer), in preferred embodiments breast cancer. The method of the invention may measure a decrease in transcription of HEYL, as described herein, or an alteration in the transcription or translation of the a regulator of HEYL or a target of HEYL (e.g. Notch 1 or Smad3). Any number of methods are available for carrying out screening assays to identify such compounds. In one approach, the method comprises contacting a cell that expresses HEYL with an agent and comparing the level of HEYL expression in the cell contacted by the agent with the level of expression in a control cell, wherein an agent that decreases the expression of HEYL thereby inhibits a neoplasia. In another approach, candidate compounds are identified that specifically bind to and alter the activity of HEYL of the invention. Methods of assaying such biological activities are known in the art and are described herein.

Potential agonists and antagonists of a HEYL nucleic acid molecule or a HEYL protein include organic molecules, peptides, peptide mimetics, polypeptides, nucleic acid molecules (e.g., double-stranded RNAs, siRNAs, antisense polynucleotides), and antibodies that bind to a nucleic acid sequence of the invention and thereby inhibit or extinguish its activity. Potential antagonists also include small molecules that bind to a HEYL nucleic acid molecule or a HEYL protein thereby preventing binding to cellular molecules with which HEYL normally interacts, such that the normal biological activity of HEYL is reduced or inhibited, for example an inhibition in the interaction of HEYL with a Smad molecule, e.g. Smad3, or an inhibition in the interaction of the Notch ICD (e.g. Notch 1 ICD) with HEYL.

Small molecules of the invention preferably have a molecular weight below 2,000 daltons, more preferably between 300 and 1,000 daltons, and still more preferably between 400 and 700 daltons. It is preferred that these small molecules are organic molecules.

Compounds that are identified as binding to a HEYL nucleic acid molecule or a HEYL protein of the invention with an affinity constant less than or equal to 10 mM are considered particularly useful in the invention. Alternatively, any in vivo protein interaction detection system, for example, any two-hybrid assay may be utilized to identify compounds that interact a HEYL nucleic acid molecule. Interacting compounds isolated by this method (or any other appropriate method) may, if desired, be further purified (e.g., by high performance liquid chromatography). Compounds isolated by any approach described herein may be used as therapeutics to treat a neoplasia in a human patient.

In addition, compounds that inhibit the expression of a HEYL nucleic acid molecule whose expression is increased in a subject having a neoplasia are also useful in the methods of the invention. Any number of methods are available for carrying out screening assays to identify new candidate compounds that alter the expression of a HEYL nucleic acid molecule.

The invention also includes novel compounds identified by the above-described screening assays. Optionally, such compounds are characterized in one or more appropriate animal models to determine the efficacy of the compound for the treatment of a neoplasia. Desirably, characterization in an animal model can also be used to determine the toxicity, side effects, or mechanism of action of treatment with such a compound. Furthermore, novel compounds identified in any of the above-described screening assays may be used for the treatment of a neoplasia in a subject. Such compounds are useful alone or, in combination with other conventional therapies known in the art.

Test Compounds and Extracts

Given the role of HEYL in all stages of breast cancer development, from pre-malignant to highly malignant and metastatic, it is a feature of the invention to identify test compounds effective in the prevention and treatment of cancer, and in particular breast cancer.

In general, compounds capable of inhibiting the growth or proliferation of a neoplasia by decreasing the expression or biological activity of a HEYL nucleic acid molecule are identified from large libraries of either natural product or synthetic (or semi-synthetic) extracts or chemical libraries according to methods known in the art. Methods for making siRNAs are known in the art and are described in the Examples. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.).

In one embodiment, test compounds of the invention are present in any combinatorial library known in the art, including: biological libraries; peptide libraries (libraries of molecules having the functionalities of peptides, but with a novel, non-peptide backbone which are resistant to enzymatic degradation but which nevertheless remain bioactive; see, e.g., Zuckermann, R. N. et al., *J. Med. Chem.* 37:2678-85, 1994); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, *Anticancer Drug Des.* 12:145, 1997).

Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad Sci.* 87:6378-6382, 1990; Felici, *J. Mol. Biol.* 222: 301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-neoplastic activity should be employed whenever possible.

In an embodiment of the invention, a high thoroughput approach can be used to screen different chemicals for their potency to affect the activity of HEYL.

Those skilled in the field of drug discovery and development will understand that the precise source of a compound or test extract is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fennentation broths, and synthetic compounds, as well as modification of existing compounds.

When a crude extract is found to alter the biological activity of HEYL, a HEYL variant, or fragment thereof, further fractionation of the positive lead extract is necessary to isolate chemical constituents responsible for the observed effect. Thus, the goal of the extraction, fractionation, and purification process is the careful characterization and identification of a chemical entity within the crude extract having anti-neoplastic activity. Methods of fractionation and purification of such heterogeneous extracts are known in the art. If desired, compounds shown to be useful agents for the treatment of a neoplasm are chemically modified according to methods known in the art.

The present invention further provides methods of treating disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neoplastic disease or disorder or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which a neoplasia may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences in order to determine the efficacy of the treatment.

Microarrays

The methods of the invention may also be used for microarray-based assays that provide for the high-throughput analysis of cancer biomarkers. The HEYL nucleic acid molecules or polypeptides of the invention are useful as hybridizable array elements in such a microarray. The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. Methods for making polypeptide microarrays are described, for example, by Ge (Nucleic Acids Res. 28:e3.i-e3.vii, 2000), MacBeath et al., (Science 289:1760-1763, 2000), Zhu et al. (Nature Genet. 26:283-289), and in U.S. Pat. No. 6,436,665, hereby incorporated by reference.

Nucleic Acid Microarrays

To produce a nucleic acid microarray oligonucleotides may be synthesized or bound to the surface of a substrate using a chemical coupling procedure and an ink jet application apparatus, as described in PCT application WO95/251116 (Baldeschweiler et al.), incorporated herein by reference. Alternatively, a gridded array may be used to arrange and link cDNA fragments or oligonucleotides to the surface of a substrate using a vacuum system, thermal, UV, mechanical or chemical bonding procedure.

A nucleic acid molecule (e.g. RNA or DNA) derived from a biological sample may be used to produce a hybridization probe as described herein. The biological samples are generally derived from a patient, preferably as a bodily fluid (such as blood, cerebrospinal fluid, phlegm, saliva, or urine) or tissue sample (e.g. a tissue sample obtained by biopsy). For some applications, cultured cells or other tissue preparations may be used. The mRNA is isolated according to standard methods, and cDNA is produced and used as a template to make complementary RNA suitable for hybridization. Such methods are described herein. The RNA is amplified in the presence of fluorescent nucleotides, and the labeled probes are then incubated with the microarray to allow the probe sequence to hybridize to complementary oligonucleotides (e.g., HEYL nucleic acid molecules) bound to the microarray.

Incubation conditions are adjusted such that hybridization occurs with precise complementary matches or with various degrees of less complementarity depending on the degree of stringency employed. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In another embodiment, hybridization will occur at 37° C. in 500 mM NaCl, 50 mM trisodium citrate, 1% SDS, 35% formamide, and 100 µg/ml denatured salmon sperm DNA (ssDNA). In yet another embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The removal of nonhybridized probes may be accomplished, for example, by washing. The washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., at least about 42° C., or at least about 68° C. In one embodiment, wash steps will occur at 25° C. in 30 mM NaCl, 3 mM trisodium citrate, and 0.1% SDS. In another embodiment, wash steps will occur at 42° C. in 15 mM NaCl, 1.5 mM trisodium citrate, and 0.1% SDS. In yet another embodiment, wash steps will occur at 68° C. in 15 mM NaCl, 1.5 mM trisodium citrate, and 0.1% SDS. Additional variations on these conditions will be readily apparent to those skilled in the art.

A detection system may be used to measure the absence, presence, and amount of hybridization for all of the distinct sequences simultaneously (e.g., Heller et al., Proc. Natl. Acad. Sci. 94:2150-2155, 1997). Preferably, a scanner is used to determine the levels and patterns of fluorescence.

Protein Microarrays

HEYL polypeptides, such as those described herein, may also be analyzed using protein microarrays. Such arrays are useful in high-throughput low-cost screens to identify peptide or candidate compounds that bind a polypeptide of the invention, or fragment thereof. Typically, protein microarrays feature a protein, or fragment thereof, bound to a solid support. Suitable solid supports include membranes (e.g., membranes composed of nitrocellulose, paper, or other material), polymer-based films (e.g., polystyrene), beads, or glass slides. For some applications, HEYL polypeptides are spotted on a substrate using any convenient method known to the skilled artisan (e.g., by hand or by inkjet printer). Preferably, such methods retain the biological activity or function of the protein bound to the substrate (e.g., HEYL antibody binding).

The protein microarray is hybridized with a detectable probe. Such probes can be polypeptide (e.g., a HEYL antibody), nucleic acid, or small molecules. For some applications, polypeptide and nucleic acid probes are derived from a biological sample taken from a patient, such as a bodily fluid (such as blood, urine, saliva, or phlegm); a homogenized tissue sample (e.g. a tissue sample obtained by biopsy); or cultured cells (e.g., lymphocytes). Probes can also include antibodies, candidate peptides, nucleic acids, or small molecule compounds derived from a peptide, nucleic acid, or chemical library. Hybridization conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual. 1998, New. York: Cold Spring Harbor Laboratories. After removal of non-specific probes, specifically bound probes are detected, for example, by fluorescence, enzyme activity (e.g., an enzyme-linked calorimetric assay), direct immunoassay, radiometric assay, or any other suitable detectable method known to the skilled artisan.

Detection of an increase in the amount of a HEYL polypeptide or a HEYL polynucleotide present in a patient sample is useful as a diagnostic for the presence of a neoplasia. Optionally, HEYL detection may be combined with the detection of other biomarkers, where the presence or level of the biomarker is correlated with the presence of a neoplasia.

Kits

The invention provides kits for the prognosis, diagnosis or monitoring of a neoplasia, such as a breast neoplasia as described herein. In one embodiment, the kit detects an alteration in the expression of a Marker (e.g., HEYL, Notch1 ICD, Notch 2 ICD, Notch 3 ICD, Notch 4 ICD, and Smad3) nucleic acid molecule relative to a reference level of expression. In another embodiment, the kit detects an alteration in the sequence of a HEYL, Notch1 ICD, Notch 2 ICD, Notch 3 ICD, Notch 4 ICD, or Smad3 nucleic acid molecule derived from a subject relative to a reference sequence. In related embodiments, the kit includes reagents for monitoring the expression of a HEYL, Notch1 ICD, Notch 2 ICD, Notch 3 ICD, Notch 4 ICD, and Smad3 nucleic acid molecule, such as primers or probes that hybridize to a HEYL, Notch or Smad cluster nucleic acid molecule.

Optionally, the kit includes directions for monitoring the nucleic acid molecule levels of a Marker in a biological sample derived from a subject. In other embodiments, the kit comprises a sterile container that contains the primer, probe, antibody, or other detection regents; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the primers or probes described herein and their use in diagnosing a neoplasia. Preferably, the kit further comprises any one or more of the reagents described in the diagnostic assays described herein. In other embodiments, the instructions include at least one of the following: description of the primer or probe; methods for using the enclosed materials for the diagnosis of a neoplasia; precautions; warnings; indications; clinical or research studies; and/or references. The instructions may be printed directly on the container (when present), or as a label applied to the container, or as a separate sheet, pamphlet, card, or folder supplied in or with the container.

EXAMPLES

Figure 1B:
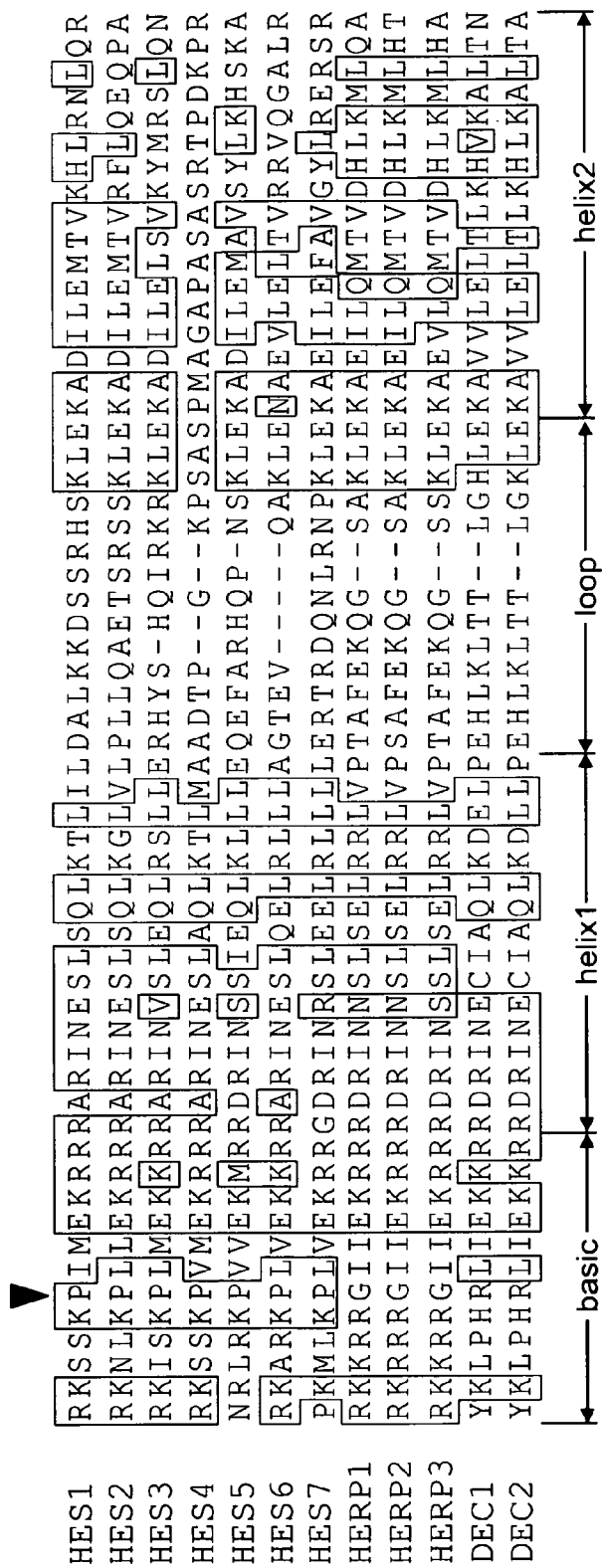
FIG. 1B discloses SEQ ID NOS 8-19, respectively, in order of appearance.
Figures 1C, 1D:
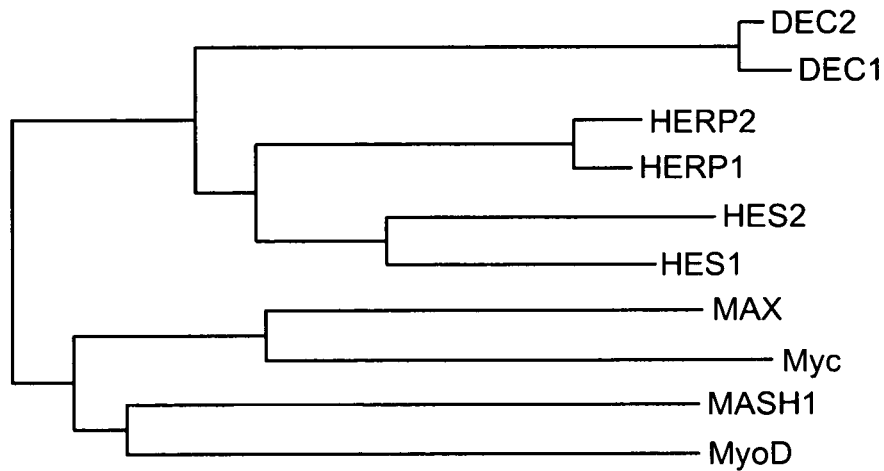
FIG. 1C discloses SEQ ID NOS 20-29, respectively, in order of appearance.

HEYL is a basic helix loop helix transcription factor that belongs to the HES-related repressor protein (HERP) family, a HES-related basic helix-loop-helix protein family. The HERP and HES family are closely functional and structurally related. The HERP family has conserved domains similar to those in the HES/E(spl) family. FIG. 1 shows a structural comparison of HES, HEYL and related family members. In addition to the homologous bHLH domain, HERP and HES share the Orange domain (12) and the tetrapeptide motif at the carboxyl terminus. However, the invariant proline residue in the basic domain and the WRPW (SEQ ID NO: 4) tetrapeptide of HES/E (spl) are replaced in HERPs by a glycine and by YRPW (SEQ ID NO: 5) (or YQPW (SEQ ID NO: 6)). Such features are also conserved in a Drosophila HERP orthologue. These structural differences define the HERP family as related to, but distinct from, HES/E (spl) (12).

Figure 2:
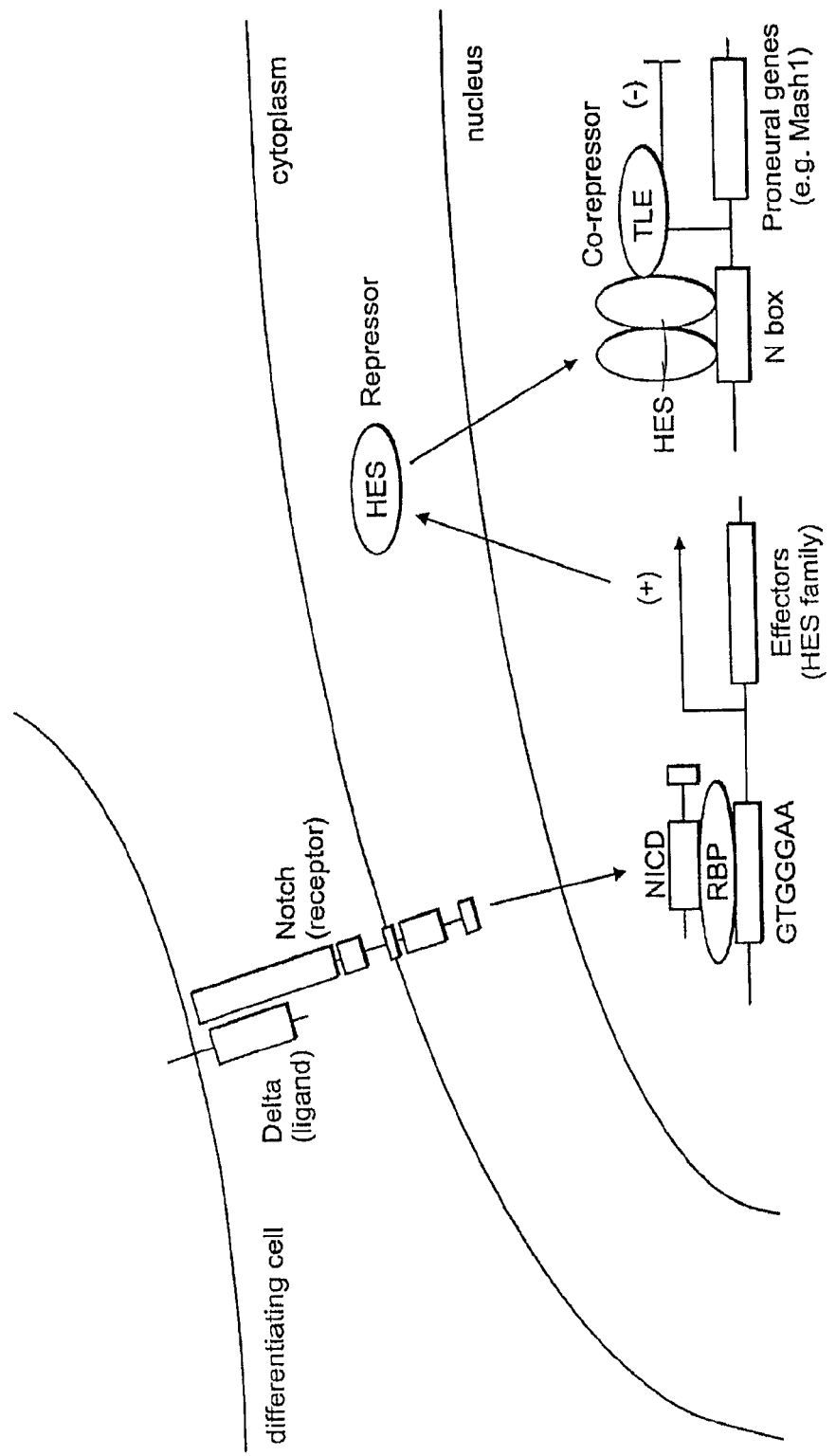
FIG. 2 shows a schematic of the Notch signaling pathway.

A schematic of the Notch signaling pathways is shown in FIG. 2. The Notch signaling pathway is involved in cell fate decisions of tissues and organs in several different organisms. The Notch gene encodes a transmembrane receptor protein. In mammals there are four members of the Notch gene family, some of which are targets for mutations that contribute to tumor development (12). Recently, growing evidence supports aberrant Notch signaling in malignant transformation. For example, Notch3 over-expression has been implicated in cases of human lung cancer (14) and activation of Notch3 in lung epithelium leads to the inhibition of epithelial differentiation (15). In a subset of human T-cell acute lymphoblastic leukemias, there is a disruption in the Notch1 gene locus that leads to activated Notch1 signaling (16).

Example 1

Cells Expressing HEYL Acquire Malignant Characteristics

Resistance to Apoptosis

Figure 3:
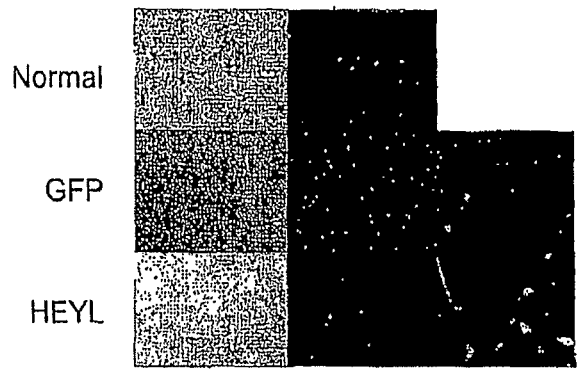
FIG. 3 shows HEYL expressing HUVEC cells show increased anti-apoptosis in growth factor depleted media.

Human umbilical vein endothelial cells (HUVEC) are an adherent endothelial cell line derived from human umbilical vein endothelium. HUVEC cells were transfected with GFP or HEYL constructs in order to create HUVEC cells that over-express HEYL. It was found that these HUVEC cells that over-express HEYL, when cultured in vitro, show an increased resistance to apoptosis when cultured in growth factor depleted medium. This is shown in FIG. 3.

Morphological Changes

Figure 4:
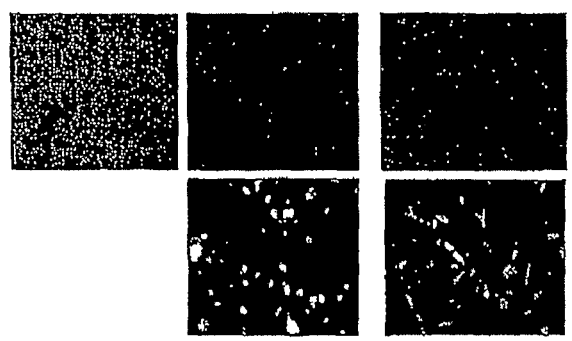
FIG. 4 shows HEYL induced morphology changes in HUVEC cells.

Further, it was shown that HEYL induces morphology changes in HUVEC cells. This is shown in FIG. 4, where normal, GFP transfected and HEYL transfected HUVEC cells were morphologically compared. FIG. 4 shows that HEYL expressing HUVEC cells appear more elongated and spread out, which are characteristics of a transformed phenotype.

Increased Invasiveness

Figure 5:
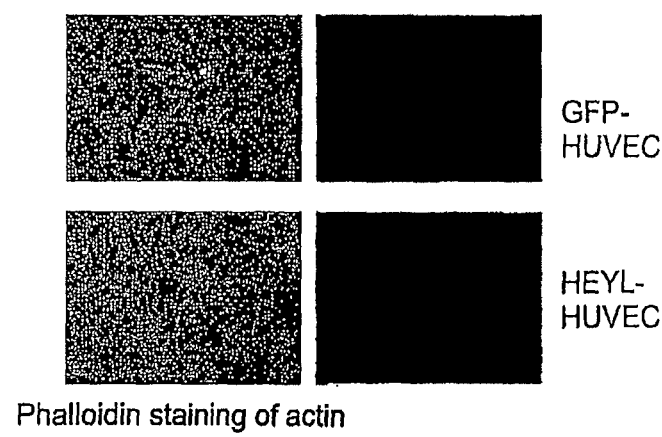
FIG. 5 shows actin rearrangement in HEYL expressing HUVEC cells.

The effect of HEYL on cell invasion was examined. First, it was found that HUVEC cells, which over-express HEYL, demonstrate a rearrangement in actin cytoskeleton, as shown in FIG. 5. Next, using a boyden chamber invasion assay to assess cell invasion through a MATRIGEL matrix, it was found that HEYL-HUVEC cells invade more efficiently through MATRIGEL as compared to the control, GFP-HUVEC cells. This is shown in FIG. 6.

Change in Adhesion Molecules and Cytoskeletal Rearrangement

The effect of HEYL on the upregulation of adhesion molecules and the fibroblast cytoskeleton was examined. Levels of VE-cadherin, Vimentin, and Claudin were examined using western blot, and vimentin staining was examined using immunohistochemistry (IHC). This is shown in FIG. 7. An upregulation of vimentin and claudin-1 was seen in HUVEC cells that overexpress HEYL. Vimentin is a mesencymal marker, and often used as a marker to indicate that a cell has undergone a transition to a transformed phenotype.

Signaling Mechanisms

Figure 9:
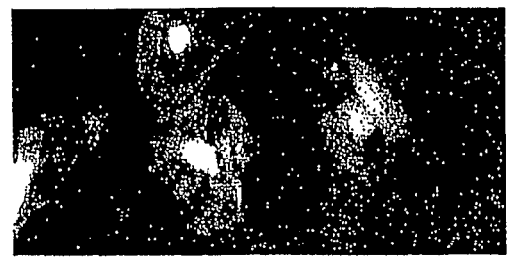
FIG. 9 shows FAK immunoflourescent staining of HEYL-HUVEC cells.

FIG. 8 presents a schematic showing possible signaling mechanisms that may underlie the HEYL induced transformation. For instance, HEYL-induced perturbation of integrin contacts may affect Focal adhesion kinase (FAK) signaling, and thus regulate and integrate a number of downstream signaling pathways and events. Panel B of FIG. 8 shows a western blot used to detect levels of FAK and phosphorylated FAK. Phosphphorylated FAK 9p-FAK) represents the signaling-active form of the protein. It was found that levels of phosphorylated FAK are increased in HUVEC cells with increased HEYL. FIG. 9 confirms that levels of signaling active FAX are increased in cells that express increased HEYL. Here, staining of phosphorylated FAK (FAKy397) in HUVEC cells is stronger in cells expressing HEYL as compared to a GFP control.

Figure 10:
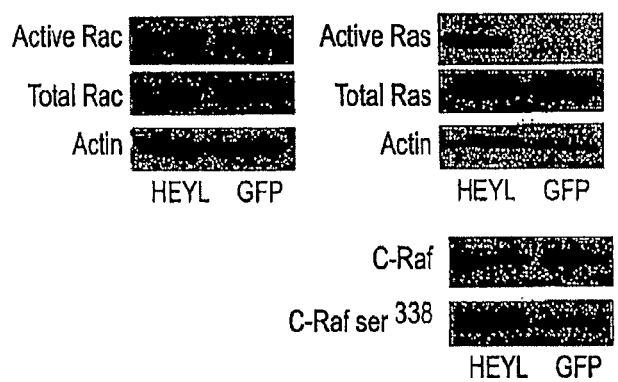
FIG. 10 shows Rac and Ras are activated in HEYL-HUVEC cells.

The effect of HEYL on the Ras and Rac signaling pathways was next examined. Levels of active Rac, total Rac, active Ras and total Ras were determined using western blot. FIG. 10 shows the results of these experiments. In cells expressing HEYL, levels of active Ras and active Rac were higher as compared to control. Further, levels of c-Raf and C-Raf-ser were higher in cells expressing HEYL, thus indicating activity of these signaling pathways in the HEYL expressing HUVEC cells.

Figure 11:
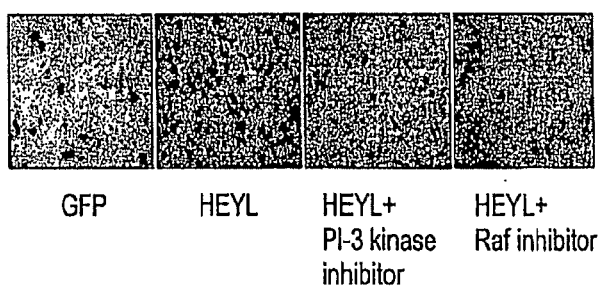
FIG. 11 shows that PI3-kinase and Raf inhibitors bloack the invasion of HEYL-HUVEC cells.

Next, because HEYL expressing HUVEC cells demonstrate increased invasinveness, the signaling pathway behind this property was examined. As such, the cells were treated with inhibitors that would block the PI-3 kinase or Raf signaling pathways, and the effect on cell invasion was determined. It was found that both the PI3-kinase and the Raf inhibitors block invasion of HEYL HUVEC cells. This is shown in FIG. 11.

Figure 12:
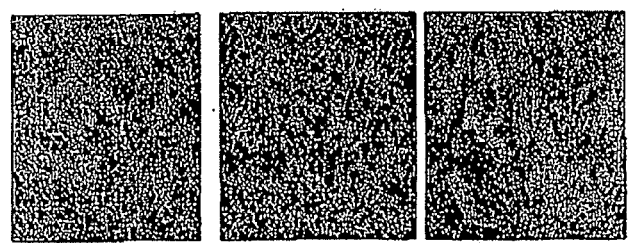
FIG. 12 shows that immunohistochemical staining showed cancer epithelial-specific expression and endothelail-specific expression. Staining is representative of more than 50 samples tested.

Finally, immunohistochemical staining with the anti-HEYL antibody revealed that HEYL showed epithelial specific expression in cancers in addition to endothelial-specific expression. The endothelial and epithelial expression is shown in FIG. 12. To confirm the epithelial expression of HEYL, RT PCR was carried out to determine the levels of HEYL mRNA in microdissected breast epithelial cells. The results are shown in FIG. 13. Taken together, the IHC staining reveals that HEYL is expressed in breast cancer epithelial cells in addition to endothelial cells.

Example 2

HEYL Increases Cell Proliferation and Cell Cycling

Figure 24:
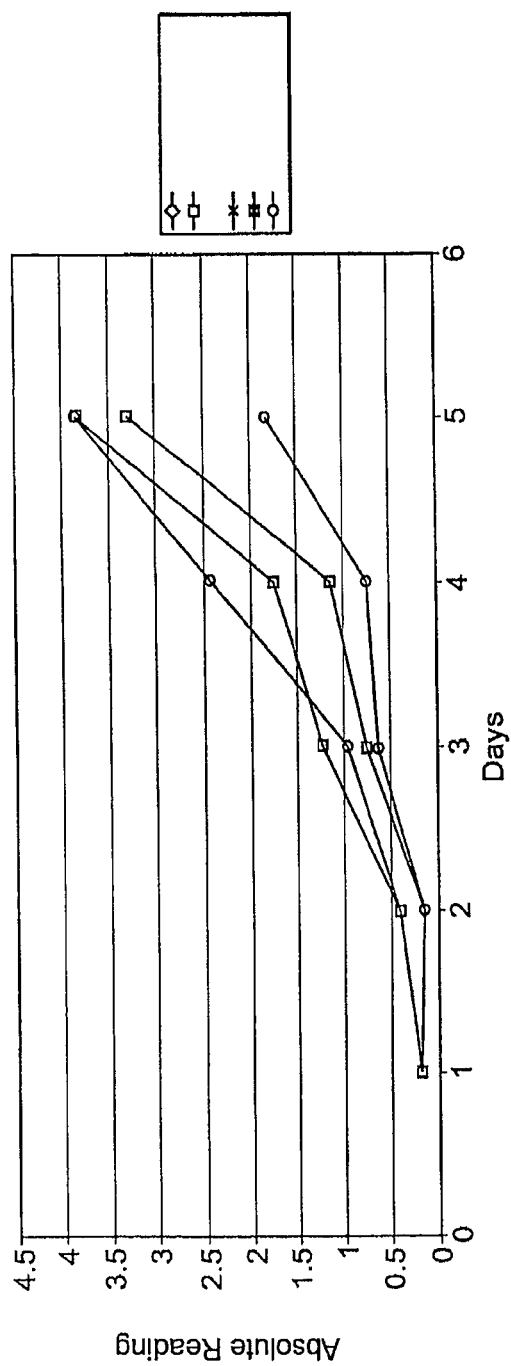
FIG. 24 shows the results of a MTT assay to measure cell growth.

The effect of HEYL on cell proliferation was examined (FIG. 24). HS578T breast cancer cells were transfected with HEYL and cell proliferation was assessed over 6 days in the presence of 2%, 5% and 10% serum. HS578T cells that were not transfected, grown under the same conditions, served as controls. The cells expressing HEYL showed an increased cell proliferation profile as compared to the HS578T control.

Figure 15:
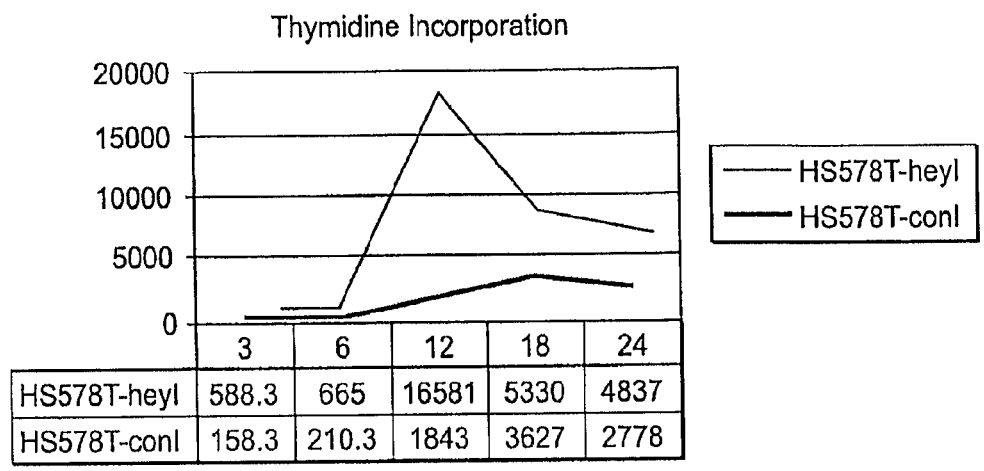
FIG. 15 shows the results of a thymidine incorporation assay for HEYL-HS578T cells.

A soft agar assay was carried out using the HT578 control and HT578 HEYL expressing cells. Growth in soft agar reflects the fact that a cell has lost its adhesion dependence and is able to grow under anchorage independent conditions, and is a hallmark of transformed growth. FIG. 14 shows the results of the soft agar assay. HEYL cells were able to form large colonies in soft agar, suggesting their transformed properties. Thymidine incorporation was determined for these cells to determine if they were alive and dividing. FIG. 15 shows the results, and indicates that HEYL expressing HS578T cells have greatly increased thymidine incorporation compared to control, indicating increased cell division.

Example 3

Expression Patterns of HEYL in Breast Cancer Clinical Samples

As discussed above, it was shown that HEYL expression in HUVEC cells can increase cell proliferation, confer strong anti-apoptosis ability and that the cells with increased HEYL elongated with actin rearrangement. Moreover, these elongated cells have increased invasion ability in Boyden chamber assay. The PI-3 kinase signal transduction pathway was shown to be involved in HEYL-induced cell invasion.

Anti-HEYL Polyclonal Antibody

To determine the expression patterns of HEYL in breast cancer clinical samples, immunohistochemical (IHC) staining of HEYL protein expression was carried out on tissue microarrays using anti-HEYL polyclonal antibody. anti-HEYL polyclonal antibody was generated by injecting HEYL sequence-specific peptide into rabbit. Rabbits were immunized with peptide conjugated to KLH (keyhole limpet hemocyanin) repeatedly. Rabbits were bled at monthly intervals to determine titer of the antibody, and when high, bled for serum collection. Western blotting showed that this antibody can recognize a specific 40 kd band, corresponding to HEYL, only in HEYL expressing cell lysates. Immunofluorescence staining detected nucleus expression of HEYL in HUVEC infected with adenovirus expressing HEYL, thus proving antibody specificity.

The anti-HEYL polyclonal antibody was used to carry out IHC staining on tissue microarrays containing breast clinical samples taken from various stages of cancer as well as non-cancerous tissue. Over 30% of breast cancer samples from early ductal carcinoma in situ to late metastatic breast cancers showed strong HEYL expression, while normal breast tissues showed no HEYL expression. Typical staining is shown in FIG. 12.

Table 1, below, summarizes the results of the IHC staining. None of the normal samples showed positive staining. For cancer samples at various stages, such as DCIS (Ductal carcinoma in situ), IDC (Invasive ductal carcinoma, Grade 1-3), LCIS (Lobular carcinoma in situ), ILC (Invasive lobular carcinoma), and LN met (Lymph node metastasis), samples with more than 10% positively stained cells were considered as positive, e.g. in 8 cases of IDC Grade 1 samples, 4 cases showed positive staining, while 3 out of these 4 cases showed over 10% of the cells positively stained. Therefore, the positive rate was determined as 37.5% (or ⅜).

TABLE 1

| Dx | Grade | Case No. | Positive | Negative | % of positive |
|---|---|---|---|---|---|
| Normal | | 16 | 0 | 16 | 0 |
| DCIS | | 30 | 18; ≤10%(9), ≥10%(9) | 12 | 30% |
| | 1 | 8 | 4; ≤10%(1), ≥10%(3) | 4 | 37.5% |
| IDC | 2 | 15 | 14; ≤10%(4), ≥10%(10) | 1 | 66.7% |
| | 3 | 14 | 12; ≤10%(7), ≥10%(5) | 2 | 35.7% |
| LCIS | 2 | 2 | 2; ≤10%(1), ≥10%(1) | 0 | 50% |
| ILC | 2 | 9 | 9; ≤10%(3), ≥10%(6) | 0 | 66.7% |
| LN Met | | 13 | 13; ≤10%(3), ≥10%(10) | 0 | 76.9% |

Example 4

Overexpression of HEYL in Breast Cancer Endothelial and Epithelial Cells

Figure 16:
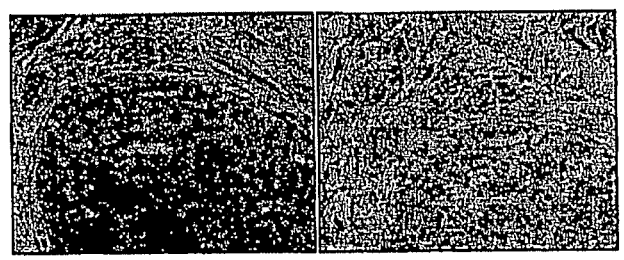
FIG. 16 shows anti-HEYL antibody staining can be blocked by immunogen peptide.

HEYL was first found to be overexpressed in breast cancer endothelial cells. Neoangiogenesis process involves complex genetic expression alterations in endothelial cells. SAGE analysis was performed on purified normal and breast cancer endothelial cells, finding that the expression of HEYL, a basic helix-loop-helix (bHLH) transcription repressor, is consistently higher in the breast cancer endothelial cells compared to normal breast tissue. The transcription factor HEYL was mainly stained in the nucleus of breast cancer epithelial cells, although mild staining of HEYL was also found in the endothelial cells. To verify the specificity of the antibody in IHC staining, HEYL immunogen peptide was used in the IHC staining experiments. The results are shown in FIG. 16, comparing the left panel, the tissue treated with the anti-HEYL antibody, to the right panel, the tissue treated with peptide block.

Example 5

HEYL Enhances Breast Cancer Development by Repressing TGF-Beta Signal Pathway It has been known for a long time that TGF-beta signal transduction is a primary tumor suppressive pathway in breast cancer. Many breast cancer cells acquire mechanisms to subvert TGF-beta's tumor suppressive effects. However, to date, the mechanisms underlying these inhibitory effects of TGF-beta remain unknown. HEYL, as described herein, may represent the first oncogene identified in breast cancer that enhances breast cancer development by repressing the TGF-beta signal pathway. The new finding provides a novel therapeutic target for prognosis, diagnosis, prevention and treatment of breast cancer.

Figure 17:
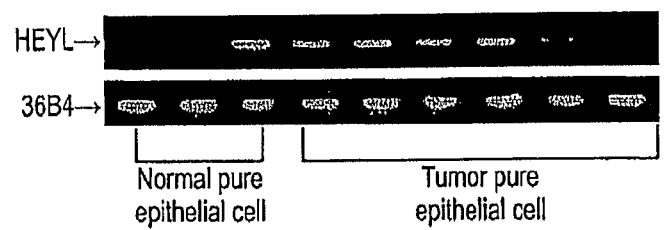
FIG. 17 shows HEYL expression can be detected in tumor epithelial cells.

To confirm that HEYL was overexpressed in breast cancer epithelial cells, HEYL mRNA expression was determined in microdissected pure epithelial cells of breast cancer. The results are shown in FIG. 17. As shown in FIG. 17, HEYL mRNA expression is evaluated in tumor pure epithelial cells and normal pure epithelial cells. The levels of expression of 36B4; a ribosomal protein gene, is used as a housekeeping gene. As shown in the Figure, HEYL mRNA was expressed at much higher levels in the malignant epithelial cells. Thus, HEYL was found to be overexpressed in both breast cancer epithelial cells and endothelial cells.

Figures 18A, 18B:
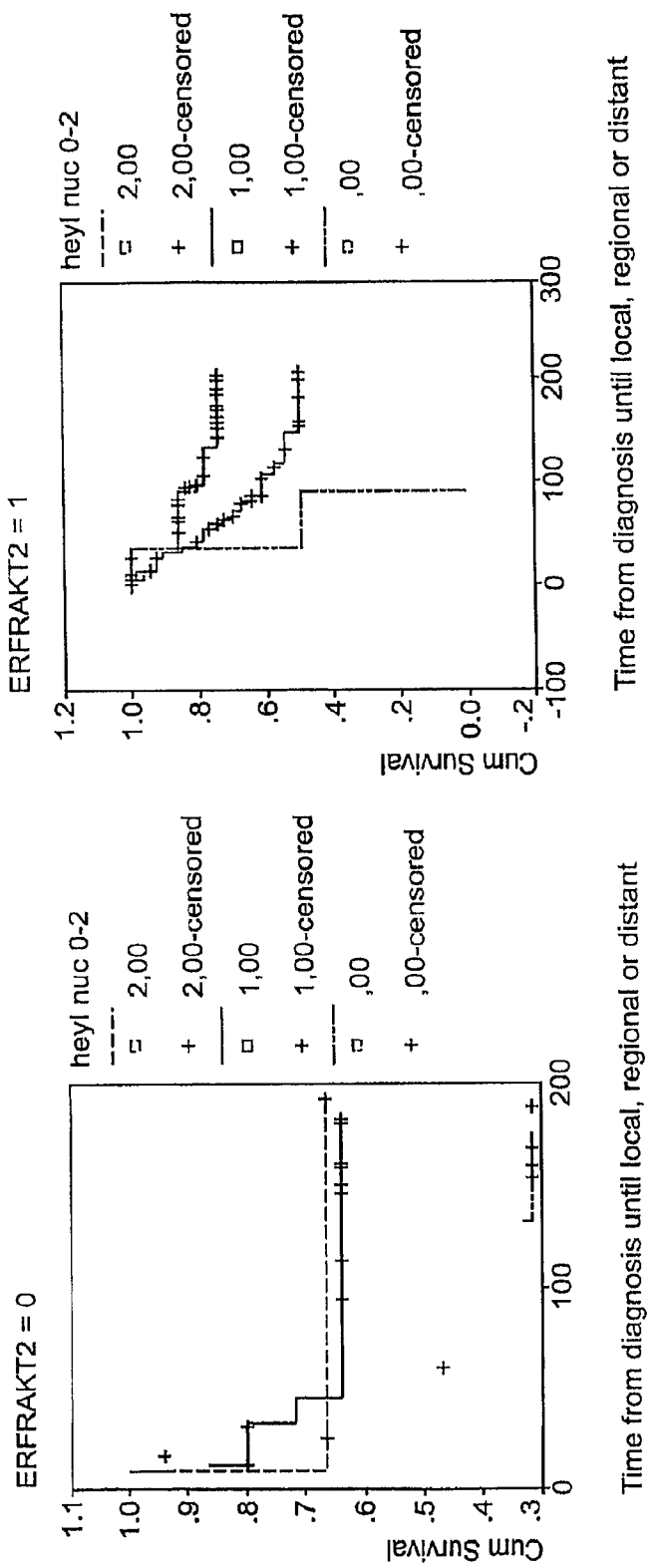
FIGS. 18 A and 18 B shows different prognosis in ER-positive and negative patients.

Next, levels of HEYL expression were further examined in clinical samples. IHC staining was performed on sets of tissue microarrays with defined clinical and molecular profiles. The correlation of HEYL expression with clinical data was analyzed. The two groups that were analyzed were estrogen receptor positive (ER+) and estrogen receptor negative (ER−) populations. The results are shown in FIG. 18. Overall, high HEYL expression (nuc 2: strong nuclear staining intensity) was associated with poor survival in ER− patients. In ER+ patients, low HEYL expression appeared to reduce survival rate. To further test the role of HEYL in breast cancer progress, IHC staining was performed on samples from two rapid autopsy patients. It was found that HEYL, in the same patient, was negative in normal and DCIS samples, but was positively stained in invasive cancer. Moreover, HEYL staining was stronger in many distant metastasis tissues. Therefore, high HEYL expression was associated with late stages of breast cancer development, thus implying that HEYL expression may be linked to poor prognosis.

Example 6

HEYL mRNA Level in Breast Cancer Samples is Elevated

Figure 19:
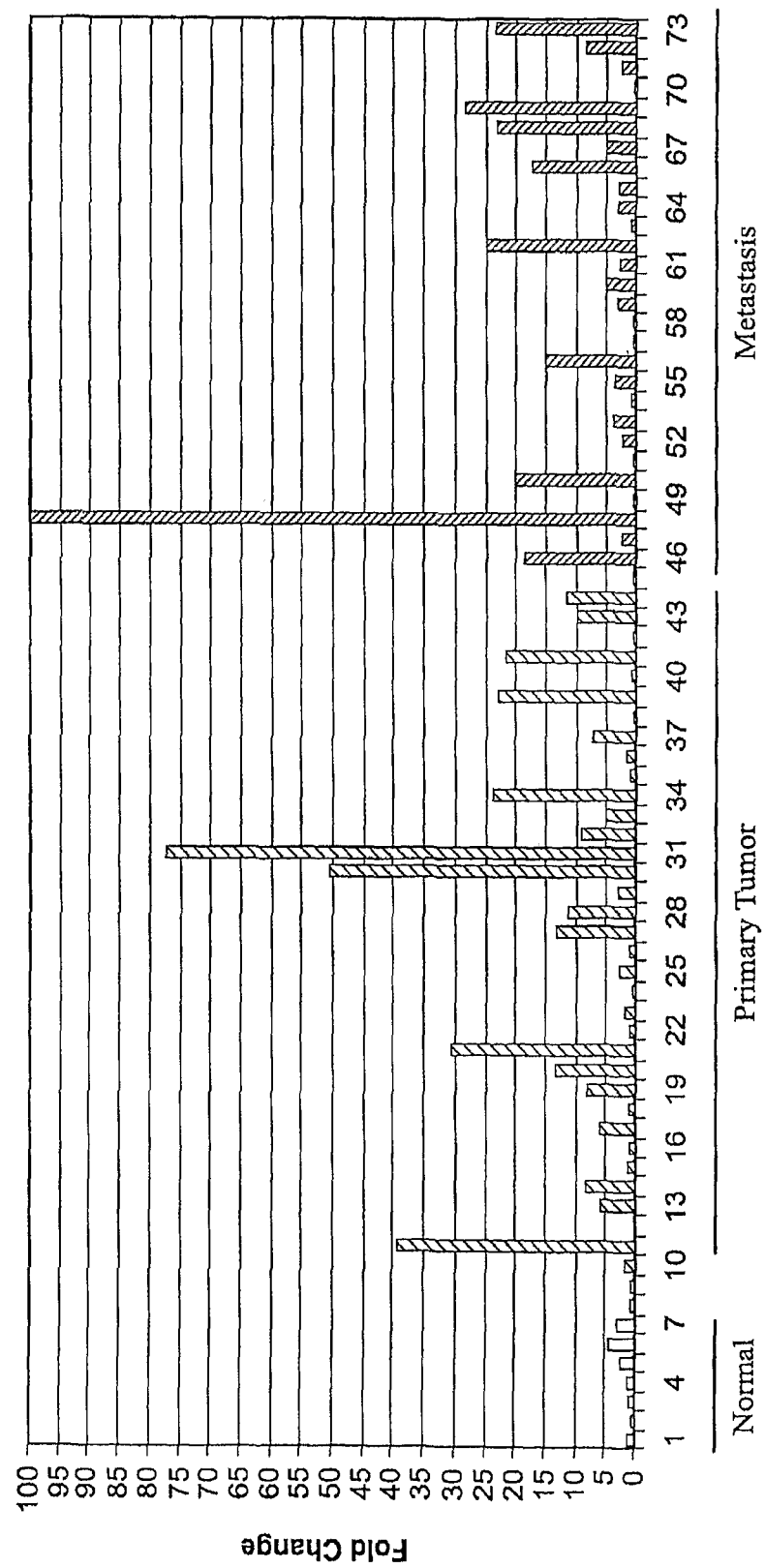
FIG. 19 is a graph showing measurement of HEYL mRNA using realtime PCR.

It has been shown herein that levels of HEYL protein are elevated in breast cancer samples, and in certain examples in tissues of distant metastasis. Thus, it was next determined if overexpressed HEYL protein was correlated with overexpressed mRNA level. Thus, HEYL mRNA expression was examined in breast cancer samples using the Realtime-polymerase chain reaction (PCR) method. The results are shown in FIG. 19. FIG. 19 shows that there is a statistically higher HEYL mRNA expression in primary and metastatic cancers than in normal breast tissues. ($p<0.05$).

Example 7

HEYL Upregulation by the Notch Pathway

Figure 20:
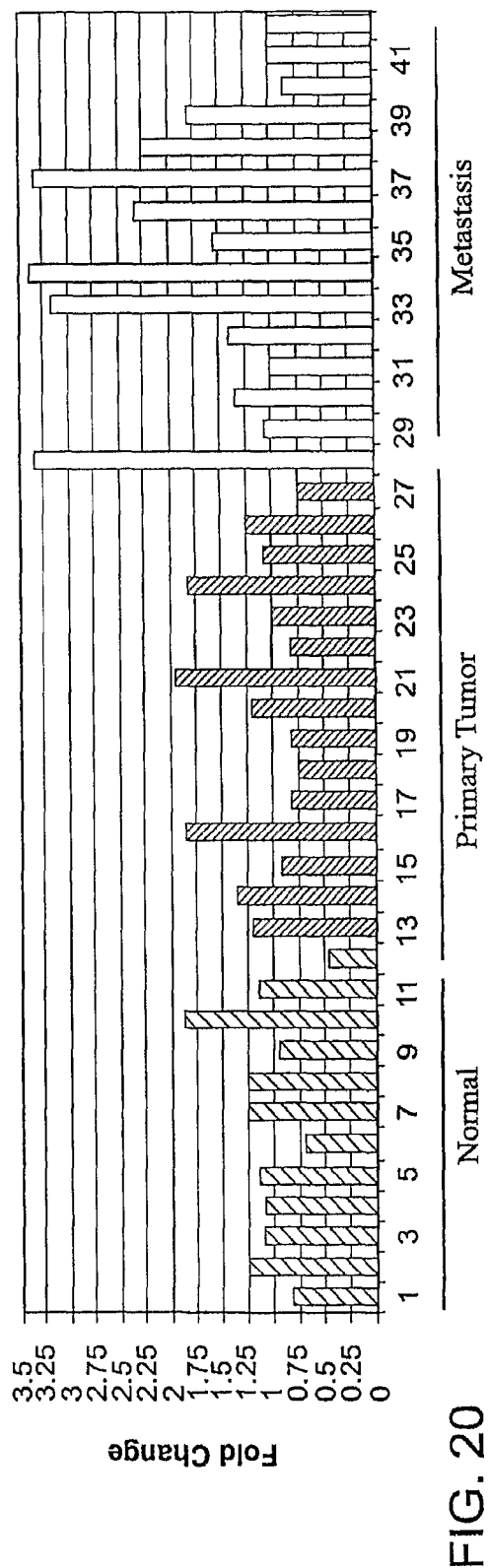
FIG. 20 is a graph showing fold change in HEYL genomic copy number using realtime PCR.

Genomic amplification is one of the mechanisms that account for gene overexpression, and refers to increases the copy number of a particular gene. The HEYL genomic copy number was measured by performing Realtime-PCR on isolated genomic DNA, as shown in FIG. 20. Only 10% of breast cancers appeared to contain more than 2 copies of HEYL. Fluorescence in situ hybridization (FISH) was performed to more accurately measure the genomic copy number of HEYL. Only 7 out of 101 samples showed gain of HEYL copy number (gain defined as >1.2-fold). But none of the 7 samples exceeded the common cutoff (>3-fold) of genomic amplification. Thus, a conclusion may be that genomic amplification was not responsible for HEYL overexpression in the analysis performed here.

Figure 21:
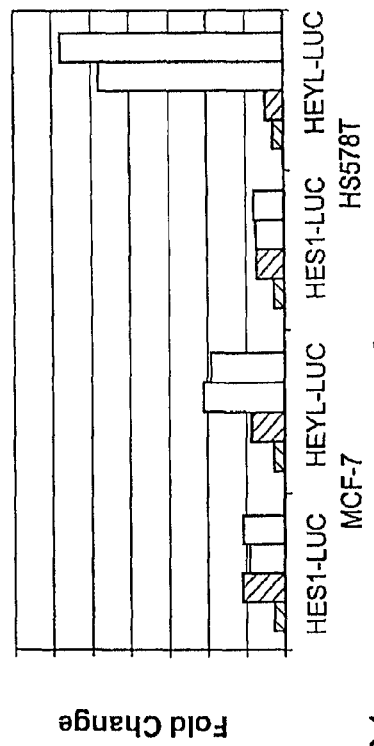
FIG. 21 is a graph showing HEYL was upregulated by Notch1.

HEYL, HEY1 and HEY2 belong to the HERP family, while HES1 is the member of a related HES family, as discussed in detail above. HES1, HEY 1 and HEY 2 have been shown to be upregulated by Notch signal transduction pathway in a number of cell types, including COST and other cell types. However, the upregulation of HEYL has been found to be weaker in those cells. (3,4) Given the significant role of the Notch pathway in breast cancer development (5) and cell-specific Notch pathway activation, it was examined whether HEYL can be unregulated by Notch in breast cancer cells. Dominant active intracellular domain (ICD) of Notch 1 was cotransfected with a HEYL promoter-luciferase vector or a HES1 promoter-luciferase vector (as a positive control) into breast cancer cell lines MCF-7 and HS578T. It was found that increasing amounts of ICD of Notch 1 can induce even more HEYL luciferase activity than the positive control HES1, suggesting that HEYL is a gene unregulated by the Notch pathway. These results are summarized in FIG. 21.

Next, different amounts of vector expressing intracellular domain of Notch 1 or control vector were transfected into HS578T cells. HEYL mRNA expression was measured 48 hours after transfection by regular PCR and Realtime-PCR. The results are shown in FIG. 22, panels A and B. As shown in both panels of FIG. 22, increasing amounts of Notch 1 increases HEYL mRNA, in a dose dependent manner. Thus, the expression of Notch1 can induced the upregulating of HEYL mRNA, confirming that HEYL is a downstream target gene activated by Notch pathway. Moreover, IHC was performed on clinical samples to check the expression correlation between Notch 1 and HEYL. A similar staining pattern was found between Notch 1 and HEYL in primary tumor samples.

Example 8

HEYL in Breast Cancer Development

Cell Transformation

The standard assay for the oncogenic activity of a gene is the NIH3T3 cell transformation assay. Retrovirus was used o overexpress HEYL in NIH3T3 cells and subcutaneously inject the cells into nude mice. NIH3T3 cells overexpressing HEYL (right side) formed much bigger tumors than the control cells 4 weeks after inoculation. The small tumors formed by control cells resulted from spontaneous transformation. The results are shown in FIG. 23.

The overexpression of HEYL in primary and metastatic breast cancer samples suggested that HEYL maybe a novel oncogene contributing to the breast cancer development. To understand its functional role, retrovirus expressing HEYL were used to infect the HS578T cell line which has little endogenous HEYL expression. The cells were then subjected to antibiotics selection and viable clones were pooled.

AS mentioned above, cell proliferation was measured by MTT (3-(4,5-dimethylthiazol-2-yl)-2,5-diphenyltetrazolium bromide) assay, shown in FIG. 24. HEYL expressing HS578T cells showed faster growth rate in normal 10% serum media than control cells and this proliferation difference was even more dramatic in reduced 2% and 5% serum containing media.

HS578T control and HEYL overexpressing cells were subcutaneously injected into nude mice to measure cell growth in vivo. Mice with representative tumors are shown in photographs in FIG. 25. Consistent with in vitro cell growth, HEYL expressing cells (right side) grew faster in vivo. (P<0.05) Moreover, the growth promoting effect of HEYL was not limited only to HS578T cells. Overexpression of HEYL in the SKBR3 breast cancer cell line also enhanced cell growth, while knocking down HEYL expression in a clinically isolated renal cell line with HEYL siRNA reduced cell growth.

Example 9

Mechanisms Behind HEYL Transformation

Figure 26:
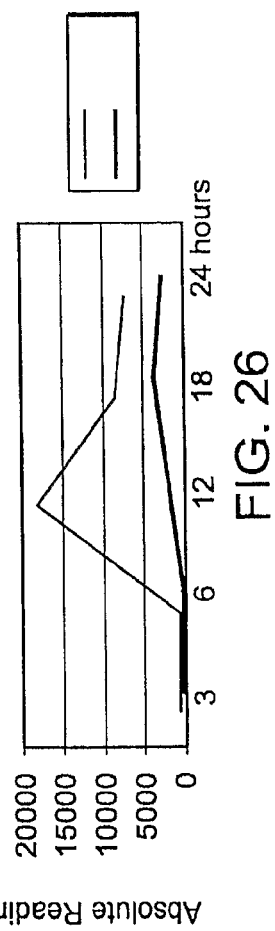
FIG. 26 is a graph showing the results of a thymidine incorporation assay.

HEYL Accelerates G1 to S Phase Transition
Accelerated cell cycle progression is often responsible for faster cell growth. To determine which stage of cell cycle was changed upon HEYL expression, 3H thymidine DNA incorporation assay was performed on both HEYL expressing and control cells. Cells were first cultured in serum free media for 2 days, thus synchronizing all cells at G1 phase. 10% serum media mixed with 3H thymidine was then incubated with cells for 3, 6, 12, 18 or 24 hours to drive the cells to simultaneously enter S phase. The radioactivity was measured at the time points. As shown in FIG. 26, HEYL expressing HS578T cells had very high 3H thymidine incorporation at 12 hours, while the control cells showed low 3H thymidine incorporation at 18 hours. The data indicates that HEYL accelerated GI to S phase transition.

Figure 27:
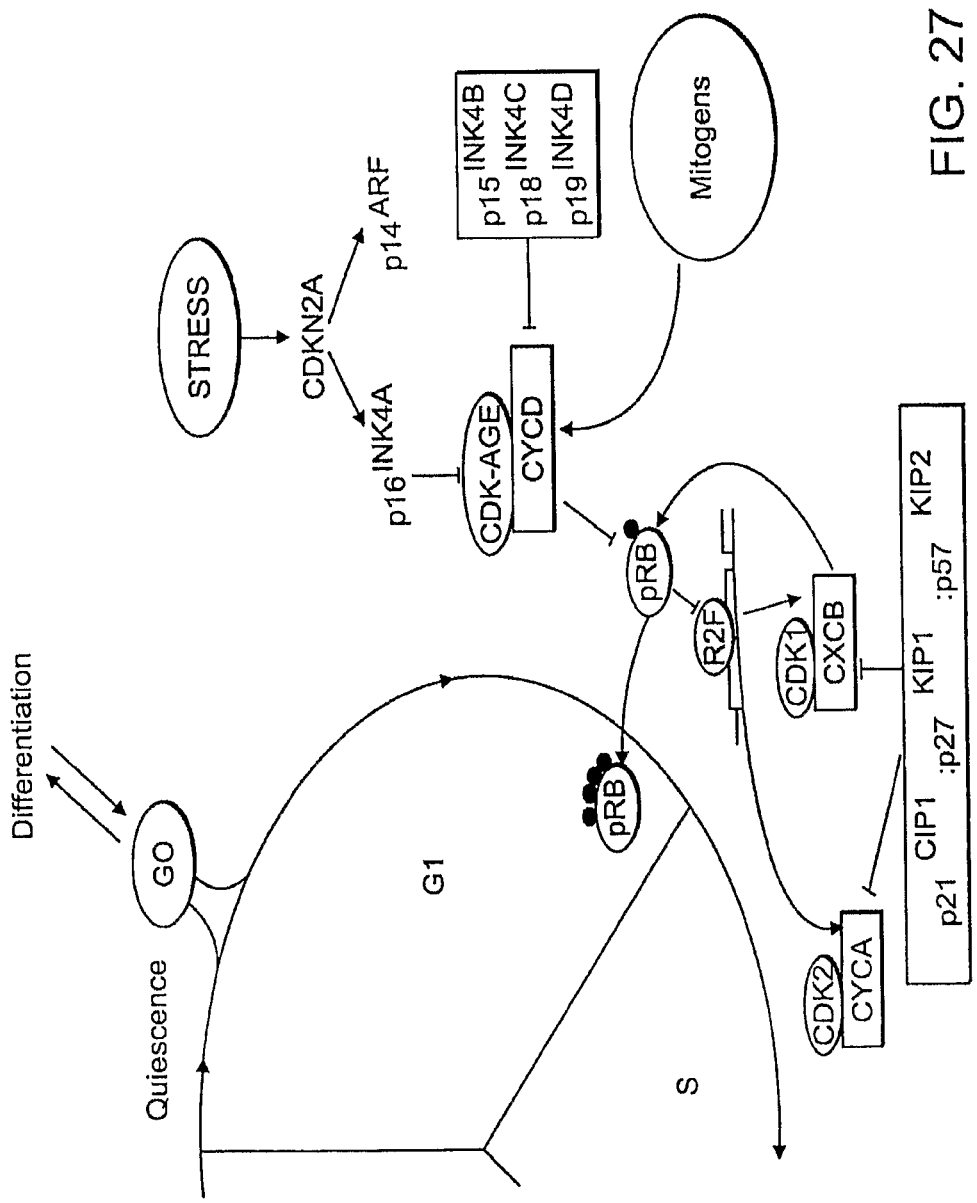
FIG. 27 shows a schematic detailing cell cycle regulation.
Figure 28:
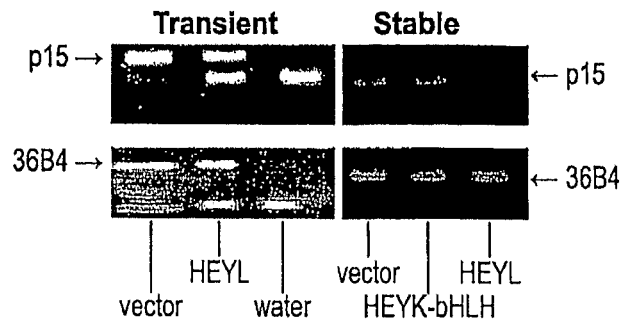
FIG. 28 shows either stable or transient HEYL expression repressed P 15 mRNA level.

HEYL Increases Cell Proliferation by Repressing p15
A schematic detailing the molecules involved in the regulation of the cell cycle is shown in FIG. 27. Genes involving G1 to S phase regulation have been intensively investigated. (6) Among those genes are well-known tumor suppressor genes (e.g. p15, p16, Rb) and oncogenes (e.g. cyclin D). Moreover, p15 has been found to be a central molecule in cell cycle regulation. Since HEYL is probably a transcriptional repressor, it is possible that HEYL may accelerate cell cycle and promote tumor formation by inhibiting a tumor suppressor gene, and thus regulating G1 to S phase transition. Accordingly, the mRNA level of many known genes that regulate G1 to S phase transition was examined by Real-time-PCR. The results showed that p15 mRNA was much lower in HEYL expressing cells than in control cells either in transient or stable transfection. Moreover, the N-terminal basic helix-loop-helix (bHLH) domain of HEYL was found to be responsible for the repression, since the truncated HEYL protein with a bHLH deletion cannot repress p15. These results are shown in FIG. 28.

Figure 30:
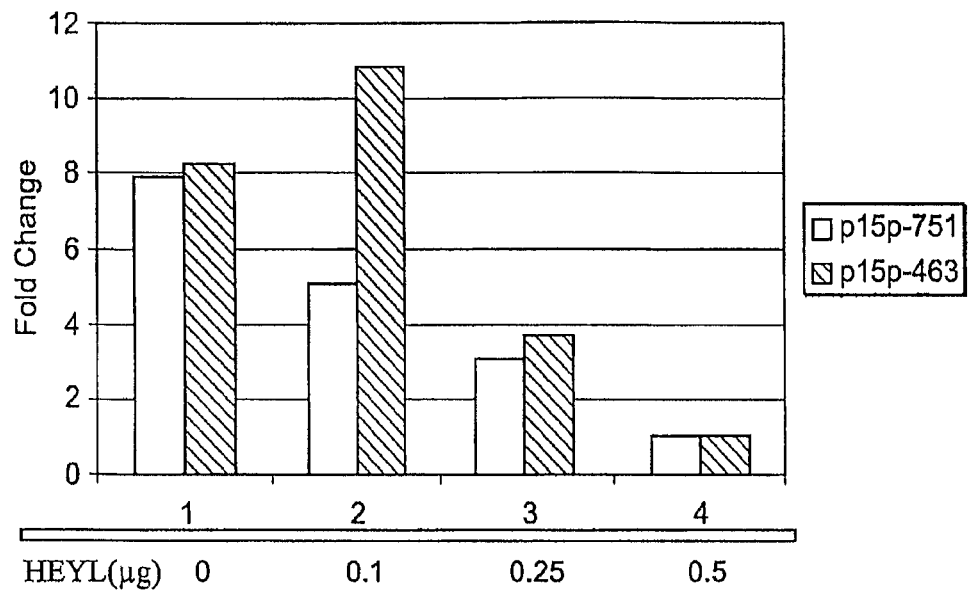
FIG. 30 shows HEYL expression repressed p15 promoter.

Further, a p15 promoter-luciferase vector was used to confirm that p15 is repressed by HEYL. The p 15 promoters of 751 by or 463 by upstream of the transcription initiation site were cloned into a PGL2 luciferase vector. (7) The luciferase vector was cotransfected with increasing amounts of HEYL expressing vector into HS578T cells. The results are shown in FIG. 30. The p15 promoter luciferase activity was repressed by all the HEYL vectors.

Figure 29:
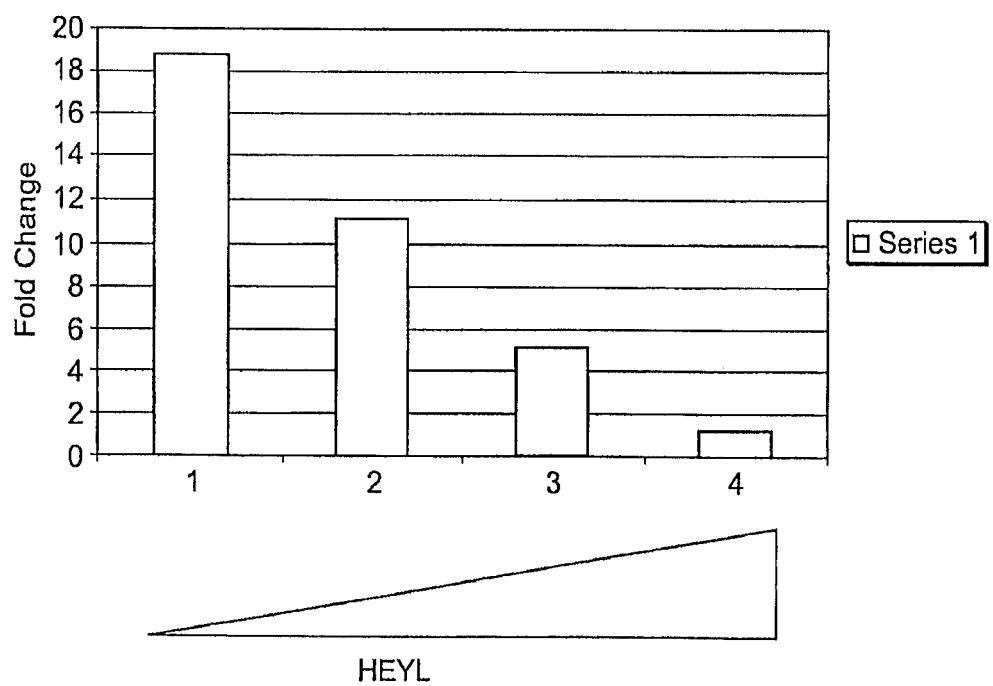
FIG. 29 shows that HEYL represses plasminogen activator inhibitor (PAI), another taget of TGF-beta.

As shown in FIG. 29, HEYL was found to repress the promoter of the plasminogen activator inhibitor (PAD), which is a known target of TGF-beta, and thus underscores the importance of the TGF-beta pathway.

Thus, taken together, the data indicates that accelerated G1 to S phase progression may account for the increased cell proliferation cell proliferation, and that HEYL may accelerate cell cycle and promote tumor formation by inhibiting p15, a tumor suppressor gene regulating G1 to S phase transition.

Example 10

HEYL may Interfere with TGF-Beta Pathway by Binding to a Smad Protein

The cytokine TGF-beta (TGF-b) causes phosphorylation of the TGF-beta receptor upon binding. The active receptor subsequently phosphorylates Smad2/3. The Smad2/3 complex interacts with Smad4 and migrates to the nucleus, where they bind to other transcription factors to regulate downstream gene expression. Many important genes involving cell cycle regulation such as p15 and p21 are upregulated by the TGF-beta pathway. Thus, the anti-proliferative effect of the TGF-b pathway is considered an important tumor suppression mechanism at the early stage of cancer development. (8) In pancreas and colon cancer, the receptor or Smad complex is frequently mutated; however in breast cancer, the mutation is very rare. As such, the mechanism by which breast cancer cells elude the anti-proliferative effects of the TGF-b pathway remains largely unknown.

Here, in an effort to understand the relationship between HEYL and the TGF-b pathway, the protein interaction database was searched. Two different high throughput approaches were found, yeast 2-hybrid and protein co-affinity purification. Both were used to identify interaction between Smad3 and HEYL. (9, 10) It is possible that HEYL may counteract the anti-proliferative effect of the TGF-b pathway by a binding interaction with Smad3.

Figure 31:
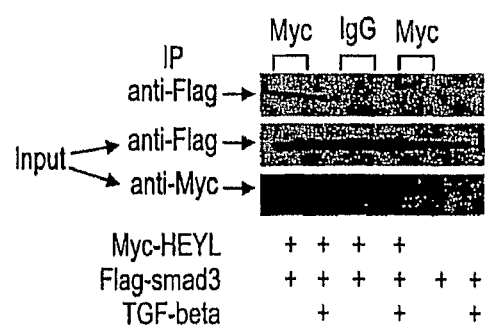
FIG. 31 shows HEYL interacted with Smad3. Immunoproecipitation/immunoblotting experiments were performed with the indicated antibodies.

The potential interaction between HEYL and Smad3 was examined by coimmunoprecipitation (coIP). Here, COS1 cells were cotransfected by myc-tag HEYL and Flag-tag Smad3 and treated with or without 4 ng/ml TGF-b. Cells were lysed, immunoprecipitated with anti myc-tag antibody and then blotted with anti flag antibody. The results are shown in FIG. 31. FIG. 31 shows that TGF beta treatment did not enhance the interaction between HEYL and Smad3.

Figure 32:
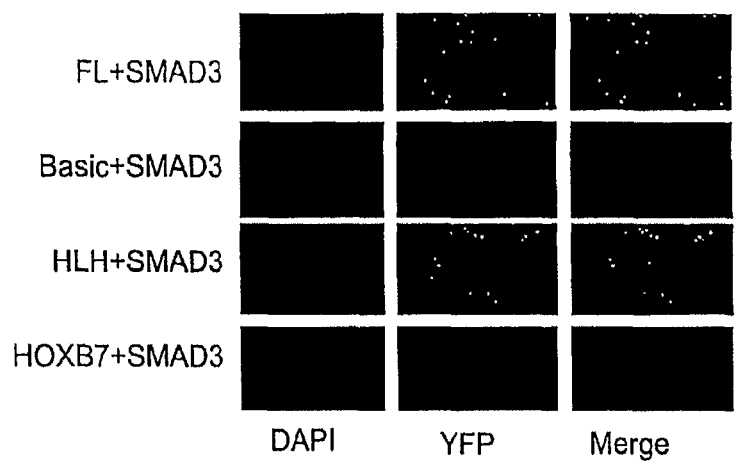
FIG. 32 shows Bimolecular Fluorescence Complementation Analysis.

Next, to test the interaction between HEYL and Smad3 in vivo, Bimolecular Fluorescence Complementation analysis was performed. This is shown in FIG. 32. In this assay, N- and C-terminal parts of Yellow Flourescent protein (YFP), were separately fused with HEYL and Smad3, respectively. If HEYL bound to Smad3 in vivo, the N- and C-terminal parts of YFP will come close in close proximity and as a result emit fluorescence. If no interaction takes place between the two molecules, no fluorescence will be emitted. The data show that HEYL interacts with Smad3 in vivo, while HoxB7, used as a negative control, did not interact with Smad3. This interaction was likely mediated by the basic domain of HEYL, since using HEYL with a deletion of the basic domain abrogated the interaction with Smad3, while using HEYL with a deletion of the HLH (helix-loop-helix) domain did not affect the interaction.

Figure 33:
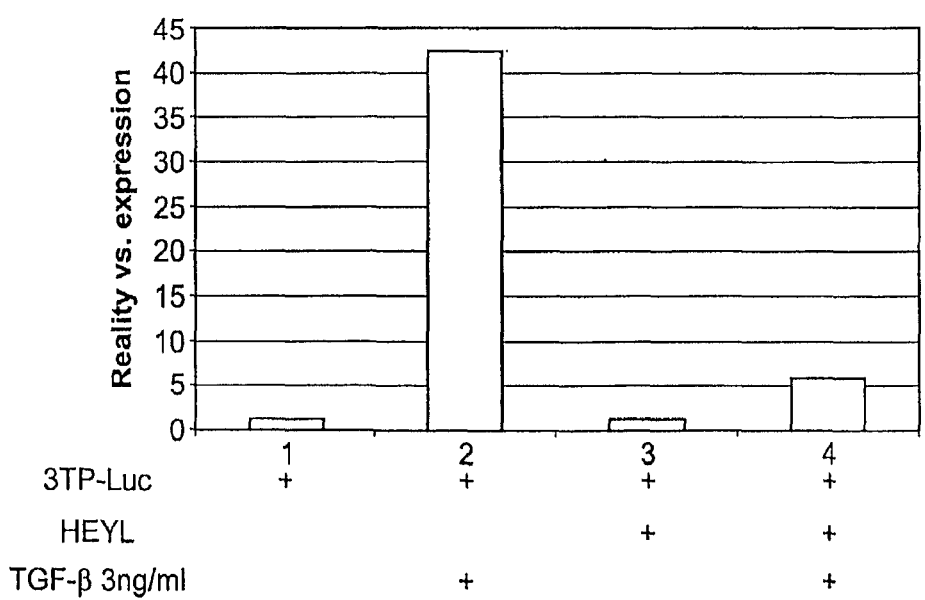
FIG. 33 shows the results of a luciferase assay where HEYL binding to Smad3 repressed TGF-b pathway activity.
Figure 34:
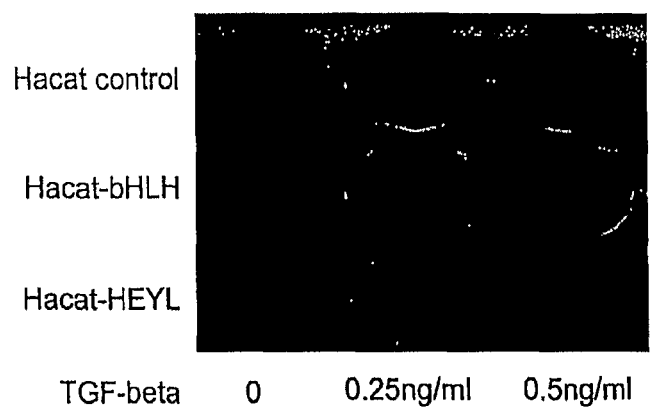
FIG. 34 shows HEYL expression rendered Hacat cell less sensitive to TGF-beta.

HEYL Effect on TGF-Beta Pathway
It was next examined if the HEYL/Smad 3 interaction had any effect on the TGF-b pathway. Thus, to determine if the interaction will interfere with TGF-b pathway activity, the gene 3TP linked to -luciferase vector, a well-known downstream target of TGF-b pathway, was co-transfected with either control or HEYL expression vector into HepG2 cell in a luciferase activity assay. The results are shown in FIG. 33: It was found that TGF-b treatment greatly increased luciferase reporter activity in control cells, while TGF-b only slightly enhanced luciferase expression in HEYL expressing cells, thus indicating the binding between HEYL and Smad3 did, in fact, interfere with TGF-b pathway activity. Next, it was examined whether the HEYL/Smad3 interaction counteracted the anti-proliferative effect of TGF-b. Hacat cells, a human keratinocyte cell line that is sensitive to the anti-proliferative effect of the TGF-b pathway, were infected by retrovirus expressing HEYL, the truncated HEYL protein with bHLH deletion, and the control vector, and treated with 0.25 ng/ml or 0.5 ng/ml TGF-b. The cells were stained with crystal violet to visualize the colonies formed by the cells. The results are shown in FIG. 34. HEYL expression rendered the cells less sensitive to TGF-b.

Taken together, the HEYL/Smad3 interaction appears to interfere with the activity and effects of the TGF-b pathway.

The data presented herein shows that HEYL interacts with Smad3 and interferes with the TGF-b pathway, an important tumor suppressive mechanism in the progression of breast cancer, and often in the early stages of breast cancer development. The discovery that HEYL represses TGF-b pathway activity reveals a novel mechanism for breast cancer to evade the cytostatic effect of TGF-b.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCES

1. C. Steidl, C. Leimeister, B. Klamt, M. Maier, I. Nanda, M. Dixon, R. Clarke, M. Schmid and M. Gessler. Characterization of the Human and Mouse HEY1, HEY2, and HEYL Genes: Cloning, Mapping, and Mutation Screening of a New bHLH Gene Family, Genomics. 2000 Jun. 1; 66(2):195-203
2. Parker B S, Argani P, Cook B P, Liangfeng H, Chartrand S D, Zhang M, Saha S, Bardelli A, Jiang Y, St Martin T B, Nacht M, Teicher B A, Klinger K W, Sukumar S, Madden SL. Alterations in vascular gene expression in invasive breast carcinoma, Cancer Res. 2004 Nov. 1; 64(21):7857-66
3. Tatsuya Iso, Larry Kedes, Yasuo Hamamori. HES and HERP families: Multiple effectors of the notch signaling pathway, J Cell Physiol. 2003 March; 194(3):237-55.
4. Osamu Nakagawa, David G. McFadden, Masayo Nakagawa, Hiromi Yanagisawa, Tonghuan Hu, Deepak Srivastava, and Eric N. Olson. Members of the HRT family of basic helix-loop-helix proteins act as transcriptional repressors downstream of Notch signaling. Proc Natl Acad Sci USA. 2000 Dec. 5; 97(25):13655-60.
5. Stylianou S, Clarke R B, Brennan K. Aberrant activation of notch signaling in human breast cancer. Cancer Res. 2006 Feb. 1; 66(3):1517-25.
6. Marcos Malumbres & Mariano Barbacid. To cycle or not to cycle: a critical decision in cancer. Nat Rev Cancer. 2001 December; 1(3):222-31.
7. Jian-Ming Li, Michael A. Nichols, Subhashini Chandrasekharan, Yue Xiong, Xiao-Fan Wang. Transforming growth factor beta activates the promoter of cyclin-dependent kinase inhibitor p15INK4B through an Sp1 consensus site, J Biol. Chem. 1995 Nov. 10; 270(45): 26750-3.
8. Siegel P M, Massague J. Cytostatic and apoptotic actions of TGF-beta in homeostasis and cancer. Nat Rev Cancer. 2003 November; 3(11):807-21.
9. Rual J F, Venkatesan K, Hao T, Hirozane-Kishikawa T, et al. Towards a proteome-scale map of the human protein-protein interaction network. Nature. 2005 Oct. 20; 437 (7062):1173-8.
10. Colland F, Jacq X, Trouplin V, Mougin C, Groizeleau C, Hamburger A, Meil A, Wojcik J, Legrain P, Gauthier J M. Functional proteomics mapping of a human signaling pathway. Genome Res. 2004 July; 14(7):1324-32.
11. Moody S E, Perez D, Pan T C, Sarkisian C J, Portocarrero C P, Sterner C J, Notorfrancesco K L, Cardiff R D, Chodosh L A. The transcriptional repressor Snail promotes mammary tumor recurrence, Cancer Cell. 2005 September; 8(3):197-209.
12. Iso T, Sartorelli V, Poizat C, Iezzi S, Wu H Y, Chung G, Kedes L, Hamamori Y. HERP, a novel heterodimer partner of HES/E(spl) in Notch signaling. Mol Cell Biol. 2001 September; 21(17):6080-9.
13. Allenspach E J, Maillard I, Aster I C and Pear W S. (2002). Cancer Biol Ther, 1, 466-76.
14. Dang T P, Eichenberger S, Gonzalez A, Olson S and Carbone D P. (2003). Oncogene, 22, 1988-97.
15. Dang T P, Gazdar A F, Virmani A K, Sepetavec T, Hande K R, Minna J D, Roberts J R and Carbone D P. (2000). J Natl Cancer Inst, 92, 1355-7.
16. Chiaramonte R, Basile A, Tassi E, Calzavara E, Cecchinato V, Rossi V, Biondi A and Comi P. (2005). Cancer Lett, 219, 113-20.
17. Andreas Fischer, Jürgen Klattig, Burkhard Kneitz, Holger Diez, Manfred Maier, Bettina Hohmann, Christoph Englert, and Manfred Gessler. Hey basic helix-loop-helix transcription factors are repressors of GATA4 and GATA6 and restrict expression of the GATA target gene ANF in fetal hearts. Mol Cell Biol. 2005 October; 25(20): 8960-70.

What is claimed is:

1. A method of diagnosing and treating a subject having breast cancer, comprising:
   obtaining a sample of breast cancer epithelial cells from the subject;
   preparing cDNA from the breast cancer epithelial cells sample;
   contacting the cDNA with amplifying PCR primers comprising SEQ ID NOs: 2 and 3;
   performing real time PCR, thereby forming an amplicon;
   comparing the rate of formation of the amplicon in the breast cancer epithelial cells cDNA sample to an appropriate control cDNA sample or to a reference level;
   diagnosing, based upon an increased rate of amplicon formation in the breast cancer epithelial cells cDNA sample, that the subject has breast cancer suitable for treatment with an agent that inhibits HEYL transcription or activity; and
   administering an effective amount of the agent to the subject, thereby treating the diagnosed breast cancer.

2. A method of diagnosing and treating a subject having breast cancer, comprising:
   obtaining a sample of breast cancer epithelial cells from the subject;
   contacting the breast cancer epithelial cells sample with an antibody that specifically binds SEQ ID NO: 1, thereby forming an antibody-HEYL polypeptide complex;
   detecting the antibody-HEYL polypeptide complex;
   comparing the level of antibody-HEYL polypeptide complex in the breast cancer epithelial cells sample to an appropriate control or to a reference level;
   diagnosing, based upon an increased level of antibody-HEYL polypeptide complex in the breast cancer epithelial cells sample, that the subject has breast cancer suitable for treatment with an agent that inhibits HEYL transcription or activity; and
   administering an effective amount of the agent to the subject, thereby treating the diagnosed breast cancer.

3. The method of claim 1, further comprising detecting a decrease in the nucleic acid or polypeptide level of Smad3 or a fragment thereof, or any combination thereof in the sample.

4. The method of claim 1, further comprising detecting a decrease in TGF-beta activity, or any combination thereof in the sample.

5. A method of increasing or decreasing the administration of a treatment of a subject diagnosed as having breast cancer, comprising:
   obtaining a sample of breast cancer epithelial cells from the subject;
   preparing cDNA from the breast cancer epithelial cells sample;
   preparing cDNA from the breast cancer epithelial cells sample;
   contacting the cDNA with amplifying PCR primers comprising SEQ ID NOs: 2 and 3;
   performing real time PCR, thereby forming an amplicon;
   comparing the rate of formation of the amplicon in the breast cancer epithelial cells cDNA sample to an appropriate control cDNA sample or to a reference level;
   administering an increased dosage of an agent that inhibits HEYL transcription or activity if the rate of formation of the amplicon in the breast cancer epithelial cells cDNA sample is greater than in the appropriate control cDNA sample or the reference level or administering a decreased dosage of an agent that inhibits HEYL transcription or activity if the rate of formation of the amplicon in the breast cancer epithelial cells cDNA sample is less than in the appropriate control cDNA sample or the reference level or administering the same dosage of an agent that inhibits HEYL transcription or activity if the rate of formation of the amplicon in the breast cancer epithelial cells cDNA sample is the same as in the appropriate control cDNA sample or the reference level.

6. The method of claim 1, wherein the agent is selected from the group consisting of a HEYL inhibitor, a Notch inhibitor, and a Smad3 inhibitor.

* * * * *

UNITED STATES PATENT AND TRADEMARK OFFICE
CERTIFICATE OF CORRECTION

PATENT NO. : 9,540,694 B2
APPLICATION NO. : 12/227552
DATED : January 10, 2017
INVENTOR(S) : Saraswati Sukumar and Liangfeng Han Page 1 of 1

It is certified that error appears in the above-identified patent and that said Letters Patent is hereby corrected as shown below:

In the Specification

Column 1 Lines 17-19, please replace the second paragraph as follows:
STATEMENT OF GOVERNMENTAL INTEREST
This invention was made with government support under grant numbers BC030941, BC030054, awarded by the National Institutes of Health, and grant number W81XWH-04-1-0382, awarded by ARMY/MRMC. The government has certain rights in the invention.

Signed and Sealed this
Thirteenth Day of February, 2018

Andrei Iancu
*Director of the United States Patent and Trademark Office*

SEQUENCE LISTING

```
<160> NUMBER OF SEQ ID NOS: 29

<210> SEQ ID NO 1
<211> LENGTH: 14
<212> TYPE: PRT
<213> ORGANISM: Unknown
<220> FEATURE:
<223> OTHER INFORMATION: Description of Unknown: HEYL peptide
```

<400> SEQUENCE: 1

Glu Pro Ser Gly Ser Asp Gly Glu Ser Asp Gly Pro Ile Asp
1               5                   10

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caactcctcc tcctcctcct                                               20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttgcaacgtg gaaatgtgtt                                               20

<210> SEQ ID NO 4
<211> LENGTH: 4
<212> TYPE: PRT
<213> ORGANISM: Unknown
<220> FEATURE:
<223> OTHER INFORMATION: Description of Unknown: HES1-7 peptide

<400> SEQUENCE: 4

Trp Arg Pro Trp
1

<210> SEQ ID NO 5
<211> LENGTH: 4
<212> TYPE: PRT
<213> ORGANISM: Unknown
<220> FEATURE:
<223> OTHER INFORMATION: Description of Unknown: HERP1-3 peptide

<400> SEQUENCE: 5

Tyr Arg Pro Trp
1

<210> SEQ ID NO 6
<211> LENGTH: 4
<212> TYPE: PRT
<213> ORGANISM: Unknown
<220> FEATURE:
<223> OTHER INFORMATION: Description of Unknown: HERP1-3 peptide

<400> SEQUENCE: 6

Tyr Gln Pro Trp
1

<210> SEQ ID NO 7
<211> LENGTH: 4
<212> TYPE: PRT
<213> ORGANISM: Unknown
<220> FEATURE:
<223> OTHER INFORMATION: Description of Unknown: HERP1-3 peptide -continued

```
<400> SEQUENCE: 7

Tyr His Ser Trp
1

<210> SEQ ID NO 8
<211> LENGTH: 59
<212> TYPE: PRT
<213> ORGANISM: Unknown
<220> FEATURE:
<223> OTHER INFORMATION: Description of Unknown: HES1 polypeptide

<400> SEQUENCE: 8

Arg Lys Ser Ser Lys Pro Ile Met Glu Lys Arg Arg Arg Ala Arg Ile
1               5                   10                  15

Asn Glu Ser Leu Ser Gln Leu Lys Thr Leu Ile Leu Asp Ala Leu Lys
            20                  25                  30

Lys Asp Ser Ser Arg His Ser Lys Leu Glu Lys Ala Asp Ile Leu Glu
        35                  40                  45

Met Thr Val Lys His Leu Arg Asn Leu Gln Arg
    50                  55

<210> SEQ ID NO 9
<211> LENGTH: 59
<212> TYPE: PRT
<213> ORGANISM: Unknown
<220> FEATURE:
<223> OTHER INFORMATION: Description of Unknown: HES2 polypeptide

<400> SEQUENCE: 9

Arg Lys Asn Leu Lys Pro Leu Leu Glu Lys Arg Arg Arg Ala Arg Ile
1               5                   10                  15

Asn Glu Ser Leu Ser Gln Leu Lys Gly Leu Val Leu Pro Leu Leu Gly
            20                  25                  30

Ala Glu Thr Ser Arg Ser Ser Lys Leu Glu Lys Ala Asp Ile Leu Glu
        35                  40                  45

Met Thr Val Arg Phe Leu Gln Glu Gln Pro Ala
    50                  55

<210> SEQ ID NO 10
<211> LENGTH: 58
<212> TYPE: PRT
<213> ORGANISM: Unknown
<220> FEATURE:
<223> OTHER INFORMATION: Description of Unknown: HES3 polypeptide

<400> SEQUENCE: 10

Arg Lys Ile Ser Lys Pro Leu Met Glu Lys Lys Arg Arg Ala Arg Ile
1               5                   10                  15

Asn Val Ser Leu Glu Gln Leu Arg Ser Leu Leu Glu Arg His Tyr Ser
            20                  25                  30

His Gln Ile Arg Lys Arg Lys Leu Glu Lys Ala Asp Ile Leu Glu Leu
        35                  40                  45

Ser Val Lys Tyr Met Arg Ser Leu Gln Asn
    50                  55

<210> SEQ ID NO 11
<211> LENGTH: 55
<212> TYPE: PRT
<213> ORGANISM: Unknown
<220> FEATURE:
<223> OTHER INFORMATION: Description of Unknown: HES4 polypeptide
```

```
<400> SEQUENCE: 11

Arg Lys Ser Ser Lys Pro Val Met Glu Lys Arg Arg Arg Ala Arg Ile
1               5                   10                  15

Asn Glu Ser Leu Ala Gln Leu Lys Thr Leu Met Ala Ala Asp Thr Pro
            20                  25                  30

Gly Lys Pro Ser Ala Ser Pro Met Ala Gly Ala Pro Ala Ser Ala Ser
        35                  40                  45

Arg Thr Pro Asp Lys Pro Arg
    50                  55

<210> SEQ ID NO 12
<211> LENGTH: 58
<212> TYPE: PRT
<213> ORGANISM: Unknown
<220> FEATURE:
<223> OTHER INFORMATION: Description of Unknown: HES5 polypeptide

<400> SEQUENCE: 12

Asn Arg Leu Arg Lys Pro Val Val Glu Lys Met Arg Arg Asp Arg Ile
1               5                   10                  15

Asn Ser Ser Ile Glu Gln Leu Lys Leu Leu Leu Glu Gln Glu Phe Ala
            20                  25                  30

Arg His Gln Pro Asn Ser Lys Leu Glu Lys Ala Asp Ile Leu Glu Met
        35                  40                  45

Ala Val Ser Tyr Leu Lys His Ser Lys Ala
    50                  55

<210> SEQ ID NO 13
<211> LENGTH: 54
<212> TYPE: PRT
<213> ORGANISM: Unknown
<220> FEATURE:
<223> OTHER INFORMATION: Description of Unknown: HES6 polypeptide

<400> SEQUENCE: 13

Arg Lys Ala Arg Lys Pro Leu Val Glu Lys Lys Arg Arg Ala Arg Ile
1               5                   10                  15

Asn Glu Ser Leu Gln Glu Leu Arg Leu Leu Leu Ala Gly Thr Glu Val
            20                  25                  30

Gln Ala Lys Leu Glu Asn Ala Glu Val Leu Glu Leu Thr Val Arg Arg
        35                  40                  45

Val Gln Gly Ala Leu Arg
    50

<210> SEQ ID NO 14
<211> LENGTH: 59
<212> TYPE: PRT
<213> ORGANISM: Unknown
<220> FEATURE:
<223> OTHER INFORMATION: Description of Unknown: HES7 polypeptide

<400> SEQUENCE: 14

Pro Lys Met Leu Lys Pro Leu Val Glu Lys Arg Arg Arg Asp Arg Ile
1               5                   10                  15

Asn Arg Ser Leu Glu Glu Leu Arg Leu Leu Leu Glu Arg Thr Arg
            20                  25                  30

Asp Gln Asn Leu Arg Asn Pro Lys Leu Glu Lys Ala Glu Ile Leu Glu
        35                  40                  45

Phe Ala Val Gly Tyr Leu Arg Glu Arg Ser Arg
    50                  55
```

<210> SEQ ID NO 15
<211> LENGTH: 57
<212> TYPE: PRT
<213> ORGANISM: Unknown
<220> FEATURE:
<223> OTHER INFORMATION: Description of Unknown: HERP1 polypeptide

<400> SEQUENCE: 15

Arg Lys Lys Arg Arg Gly Ile Ile Glu Lys Arg Arg Asp Arg Ile
1               5                   10                  15

Asn Asn Ser Leu Ser Glu Leu Arg Arg Leu Val Pro Thr Ala Phe Glu
            20                  25                  30

Lys Gln Gly Ser Ala Lys Leu Glu Lys Ala Glu Ile Leu Gln Met Thr
        35                  40                  45

Val Asp His Leu Lys Met Leu Gln Ala
    50                  55

<210> SEQ ID NO 16
<211> LENGTH: 57
<212> TYPE: PRT
<213> ORGANISM: Unknown
<220> FEATURE:
<223> OTHER INFORMATION: Description of Unknown: HERP2 polypeptide

<400> SEQUENCE: 16

Arg Lys Arg Arg Arg Gly Ile Ile Glu Lys Arg Arg Asp Arg Ile
1               5                   10                  15

Asn Asn Ser Leu Ser Glu Leu Arg Arg Leu Val Pro Ser Ala Phe Glu
            20                  25                  30

Lys Gln Gly Ser Ala Lys Leu Glu Lys Ala Glu Ile Leu Gln Met Thr
        35                  40                  45

Val Asp His Leu Lys Met Leu His Thr
    50                  55

<210> SEQ ID NO 17
<211> LENGTH: 57
<212> TYPE: PRT
<213> ORGANISM: Unknown
<220> FEATURE:
<223> OTHER INFORMATION: Description of Unknown: HERP3 polypeptide

<400> SEQUENCE: 17

Arg Lys Lys Arg Arg Gly Ile Ile Glu Lys Arg Arg Asp Arg Ile
1               5                   10                  15

Asn Ser Ser Leu Ser Glu Leu Arg Arg Leu Val Pro Thr Ala Phe Glu
            20                  25                  30

Lys Gln Gly Ser Ser Lys Leu Glu Lys Ala Glu Val Leu Gln Met Thr
        35                  40                  45

Val Asp His Leu Lys Met Leu His Ala
    50                  55

<210> SEQ ID NO 18
<211> LENGTH: 57
<212> TYPE: PRT
<213> ORGANISM: Unknown
<220> FEATURE:
<223> OTHER INFORMATION: Description of Unknown: DEC1 polypeptide

<400> SEQUENCE: 18

Tyr Lys Leu Pro His Arg Leu Ile Glu Lys Lys Arg Arg Asp Arg Ile
1               5                   10                  15

Asn Glu Cys Ile Ala Gln Leu Lys Asp Leu Leu Pro Glu His Leu Lys
            20                  25                  30

Leu Thr Thr Leu Gly His Leu Glu Lys Ala Val Val Leu Glu Leu Thr
        35                  40                  45

Leu Lys His Val Lys Ala Leu Thr Asn
    50                  55

<210> SEQ ID NO 19
<211> LENGTH: 57
<212> TYPE: PRT
<213> ORGANISM: Unknown
<220> FEATURE:
<223> OTHER INFORMATION: Description of Unknown: DEC2 polypeptide

<400> SEQUENCE: 19

Tyr Lys Leu Pro His Arg Leu Ile Glu Lys Arg Arg Asp Arg Ile
1               5                   10                  15

Asn Glu Cys Ile Ala Gln Leu Lys Asp Leu Leu Pro Glu His Leu Lys
            20                  25                  30

Leu Thr Thr Leu Gly His Leu Glu Lys Ala Val Val Leu Glu Leu Thr
        35                  40                  45

Leu Lys His Leu Lys Ala Leu Thr Ala
    50                  55

<210> SEQ ID NO 20
<211> LENGTH: 8
<212> TYPE: PRT
<213> ORGANISM: Unknown
<220> FEATURE:
<223> OTHER INFORMATION: Description of Unknown: HES1 peptide

<400> SEQUENCE: 20

Ser Met Trp Arg Pro Trp Arg Asn
1               5

<210> SEQ ID NO 21
<211> LENGTH: 6
<212> TYPE: PRT
<213> ORGANISM: Unknown
<220> FEATURE:
<223> OTHER INFORMATION: Description of Unknown: HES2 peptide

<400> SEQUENCE: 21

Gly Leu Trp Arg Pro Trp
1               5

<210> SEQ ID NO 22
<211> LENGTH: 6
<212> TYPE: PRT
<213> ORGANISM: Unknown
<220> FEATURE:
<223> OTHER INFORMATION: Description of Unknown: HES3 peptide

<400> SEQUENCE: 22

Arg Val Trp Arg Pro Trp
1               5

<210> SEQ ID NO 23
<211> LENGTH: 8
<212> TYPE: PRT
<213> ORGANISM: Unknown
<220> FEATURE:
<223> OTHER INFORMATION: Description of Unknown: HES4 peptide

```
<400> SEQUENCE: 23

Gly Pro Trp Arg Pro Trp Leu Arg
1               5

<210> SEQ ID NO 24
<211> LENGTH: 6
<212> TYPE: PRT
<213> ORGANISM: Unknown
<220> FEATURE:
<223> OTHER INFORMATION: Description of Unknown: HES5 peptide

<400> SEQUENCE: 24

Gly Leu Trp Arg Pro Trp
1               5

<210> SEQ ID NO 25
<211> LENGTH: 6
<212> TYPE: PRT
<213> ORGANISM: Unknown
<220> FEATURE:
<223> OTHER INFORMATION: Description of Unknown: HES6 peptide

<400> SEQUENCE: 25

Ser Val Trp Arg Pro Trp
1               5

<210> SEQ ID NO 26
<211> LENGTH: 7
<212> TYPE: PRT
<213> ORGANISM: Unknown
<220> FEATURE:
<223> OTHER INFORMATION: Description of Unknown: HES7 peptide

<400> SEQUENCE: 26

Ala Phe Trp Arg Pro Trp Pro
1               5

<210> SEQ ID NO 27
<211> LENGTH: 13
<212> TYPE: PRT
<213> ORGANISM: Unknown
<220> FEATURE:
<223> OTHER INFORMATION: Description of Unknown: HERP1 peptide

<400> SEQUENCE: 27

Lys Pro Tyr Gln Pro Trp Gly Thr Glu Val Gly Ala Phe
1               5                   10

<210> SEQ ID NO 28
<211> LENGTH: 13
<212> TYPE: PRT
<213> ORGANISM: Unknown
<220> FEATURE:
<223> OTHER INFORMATION: Description of Unknown: HERP2 peptide

<400> SEQUENCE: 28

Lys Pro Tyr Arg Pro Trp Gly Thr Glu Ile Gly Ala Phe
1               5                   10

<210> SEQ ID NO 29
<211> LENGTH: 16
<212> TYPE: PRT
<213> ORGANISM: Unknown
<220> FEATURE:
<223> OTHER INFORMATION: Description of Unknown: HERP3 peptide
```

```
<400> SEQUENCE: 29

Val Phe Tyr His Ser Trp Val Ser Glu Ile Thr Glu Ile Gly Ala Phe
1               5                   10                  15
```